(12) United States Patent
Blankesteijn et al.

(10) Patent No.: US 8,598,122 B2
(45) Date of Patent: Dec. 3, 2013

(54) ANTAGONISTIC PEPTIDES FOR FRIZZLED-1 AND FRIZZLED-2

(75) Inventors: Wessel Matthijs Blankesteijn, Maastricht (NL); Hilde Laeremans, Maastricht (NL); Tilman Mathias Hackeng, Maastricht (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 13/138,537

(22) PCT Filed: Feb. 18, 2010

(86) PCT No.: PCT/EP2010/052058
§ 371 (c)(1),
(2), (4) Date: Sep. 23, 2011

(87) PCT Pub. No.: WO2010/100035
PCT Pub. Date: Sep. 10, 2010

(65) Prior Publication Data
US 2012/0014876 A1 Jan. 19, 2012

(30) Foreign Application Priority Data
Mar. 5, 2009 (EP) .................................... 09154475

(51) Int. Cl.
A61K 38/00 (2006.01)
A61K 38/10 (2006.01)
A61P 9/00 (2006.01)
A61P 43/00 (2006.01)
A61P 17/00 (2006.01)
C12N 5/00 (2006.01)
C12N 5/02 (2006.01)

(52) U.S. Cl.
USPC ......... 514/16.4; 514/1.1; 514/16.5; 514/18.6; 514/21.5; 435/375

(58) Field of Classification Search
None
See application file for complete search history.

(56) References Cited

U.S. PATENT DOCUMENTS

2005/0153887 A1    7/2005  Lu et al.
2006/0019890 A1 *  1/2006  Kapoun et al. ................. 514/12

(Continued)

FOREIGN PATENT DOCUMENTS

CA     2353804          1/2003
CA     2353804 A1   *   1/2003

(Continued)

OTHER PUBLICATIONS

Oikawa et al, "Cloning and sequence analysis of cDNA encoding a precursor for human atrial natriuretic polypeptide," Nature 309:724-726 (1984).*

(Continued)

*Primary Examiner* — Marcela M Cordero Garcia
*Assistant Examiner* — Thea D' Ambrosio
(74) *Attorney, Agent, or Firm* — TraskBritt

(57) ABSTRACT

The invention is in the field of molecular medicine. It provides antagonistic compounds for frizzled 1 and/or frizzled-2 receptors, which may be useful in molecular imaging of the wound healing process after myocardial infarction and in therapeutic intervention into wound healing after remodeling of the heart, thereby ameliorating the consequences of myocardial infarction. The invention provides a method for antagonizing frizzled-1 or frizzled-2 receptors, wherein the receptor is contacted with a composition comprising a linear fragment of Wnt3(a) or Wnt5a or a functional analogue thereof, which comprises at least one cysteine residue, one threonine residue, one aspartic acid residue and one glycine residue.

4 Claims, 25 Drawing Sheets

(56) References Cited

U.S. PATENT DOCUMENTS

| | | |
|---|---|---|
| 2006/0115460 A1* | 6/2006 | Naughton .................. 424/93.21 |
| 2006/0140916 A1* | 6/2006 | Siani-Rose et al. .......... 424/93.7 |
| 2008/0207521 A1 | 8/2008 | Andersson |
| 2010/0137201 A1 | 6/2010 | Ferguson et al. |

FOREIGN PATENT DOCUMENTS

| | | |
|---|---|---|
| WO | WO0021555 | 4/2000 |
| WO | WO2004091647 | 10/2004 |
| WO | WO2006130082 | 12/2006 |
| WO | WO 2006130082 A1 * | 12/2006 |
| WO | WO2008001113 | 1/2008 |
| WO | WO 2008001113 A2 * | 1/2008 |
| WO | WO2008099174 | 8/2008 |
| WO | WO2010100035 | 9/2010 |

OTHER PUBLICATIONS

NCBI Database, Accession No. AAH74783 (cited in US 2006/0019890), "WNT5A protein [*Homo sapiens*]", 2 pages (2006).*
BLAST Alignment between present invention's SEQ ID No. 7 and AAH74783 (conducted on Jan. 21, 2013).*
BLAST alignment between present invention's SEQ ID No. 7 and Ferguson's SEQ ID No. 1 (WO 2008/001113) (conducted on Jan. 21, 2013).*
PCT International Preliminary Report on Patentability, PCT/US2010/052058, dated Sep. 6, 2011.
PCT International Search Report, PCT/EP2010/052058, dated Jul. 22, 2010.
Laeremans et al., Development of an assay system for Frizzled receptor ligands, Naunyn-Schmiedeberg's Archives of Pharmacology, Apr. 2007, pp. 147-148, vol. 375, No. 2, Lunteren, Netherlands.
Brown et al., The Wnt3A palmitoylation site is required for high affinity Frizzled binding, Developmental Biology, Jul. 1, 2006, p. 429, vol. 295, No. 1, Academic Press, New York, NY, US.
Portilho et al., A soluble and active form of Wnt-3a protein is involved in myogenic differentiation after cholesterol depletion, FEBS Letters, Nov. 26, 2007, pp. 5787-5795, vol. 581, No. 30, Elsevier, Amsterdam, Netherlands.
PCT Written Opinion, PCT/2010/052058, dated Jul. 22, 2010.

* cited by examiner

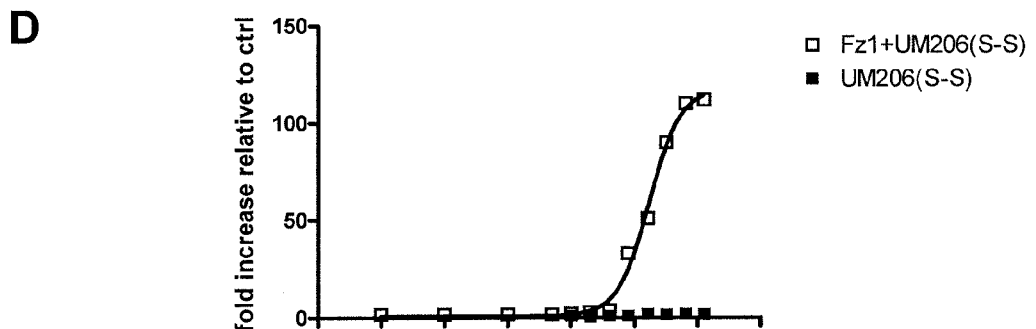
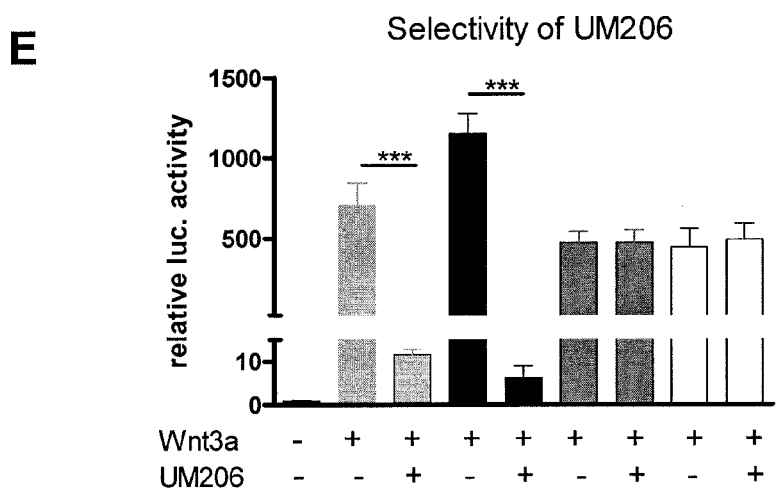
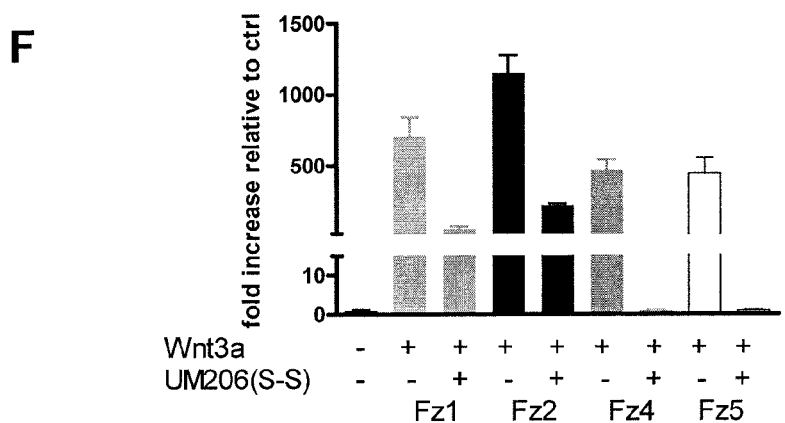
FIG. 3 (continued)

Figure 4:
A.
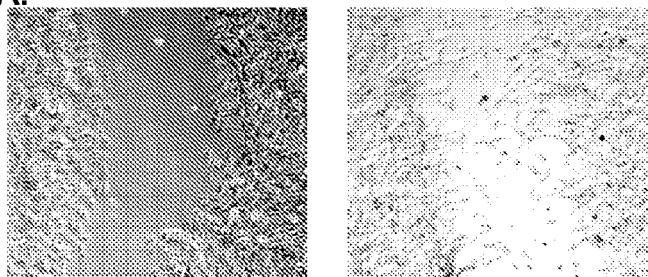
B.
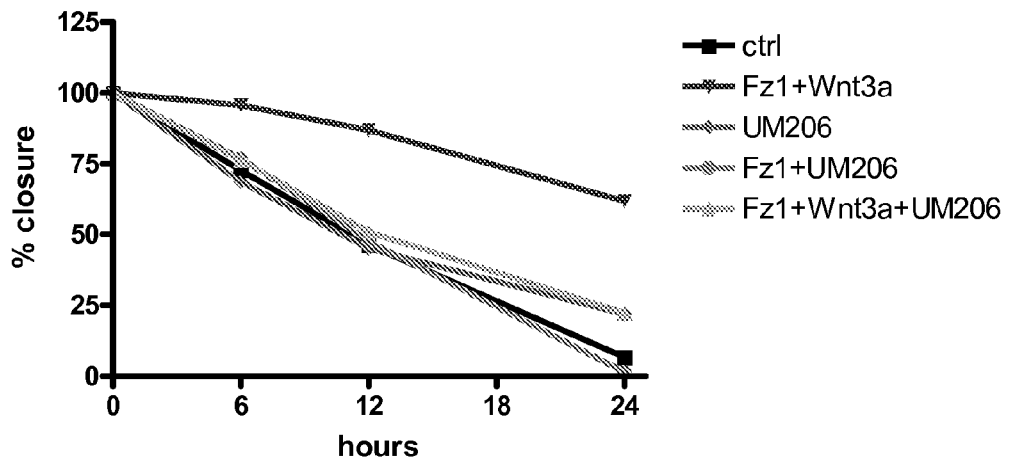
C.
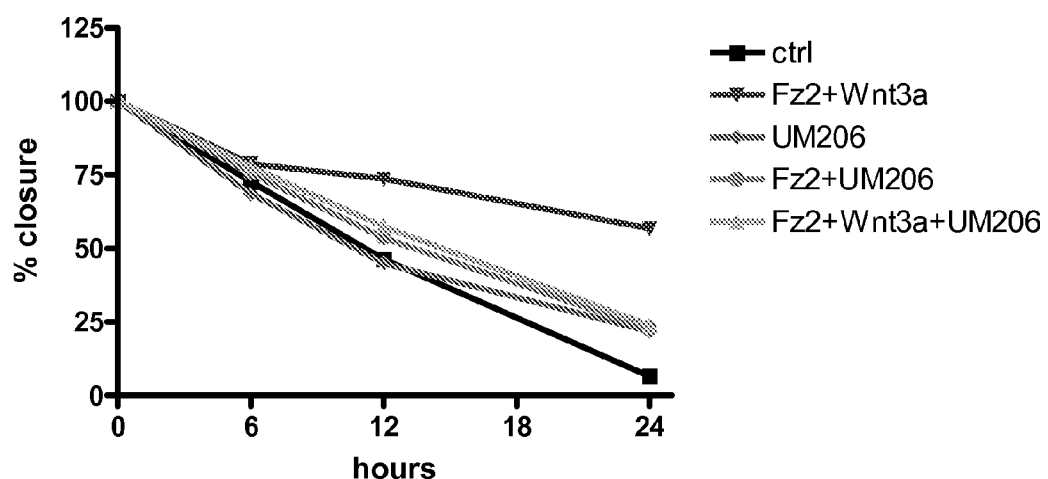

Figure 5
A.
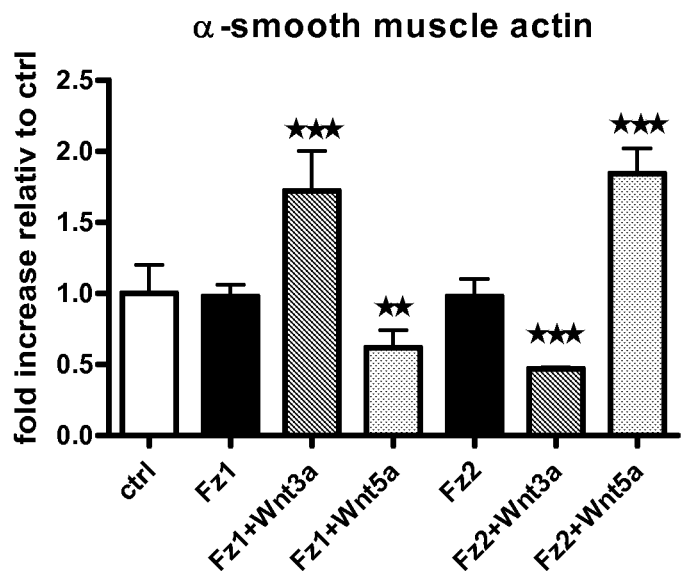
(p-values: ★★ p<0.01, ★★★ p<0.001)
B
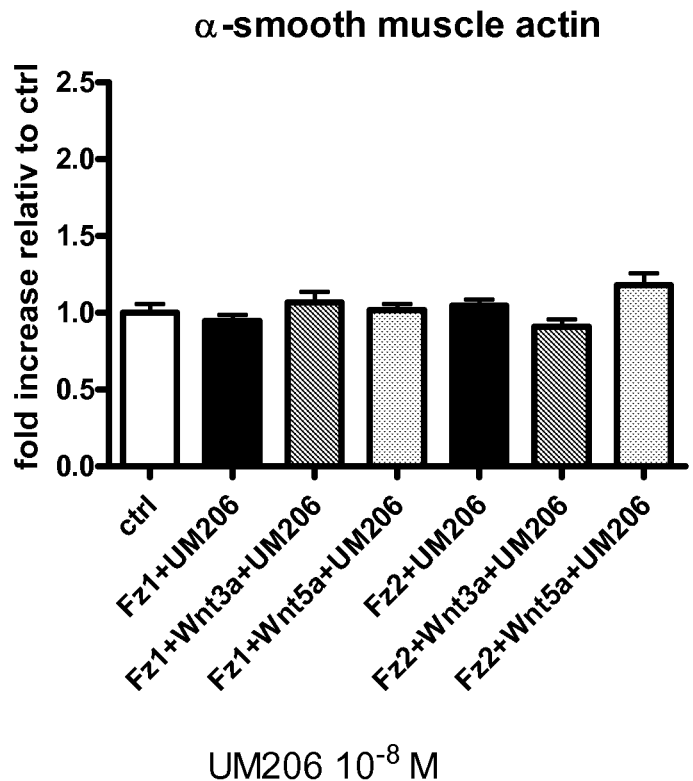
UM206 $10^{-8}$ M Figure 6
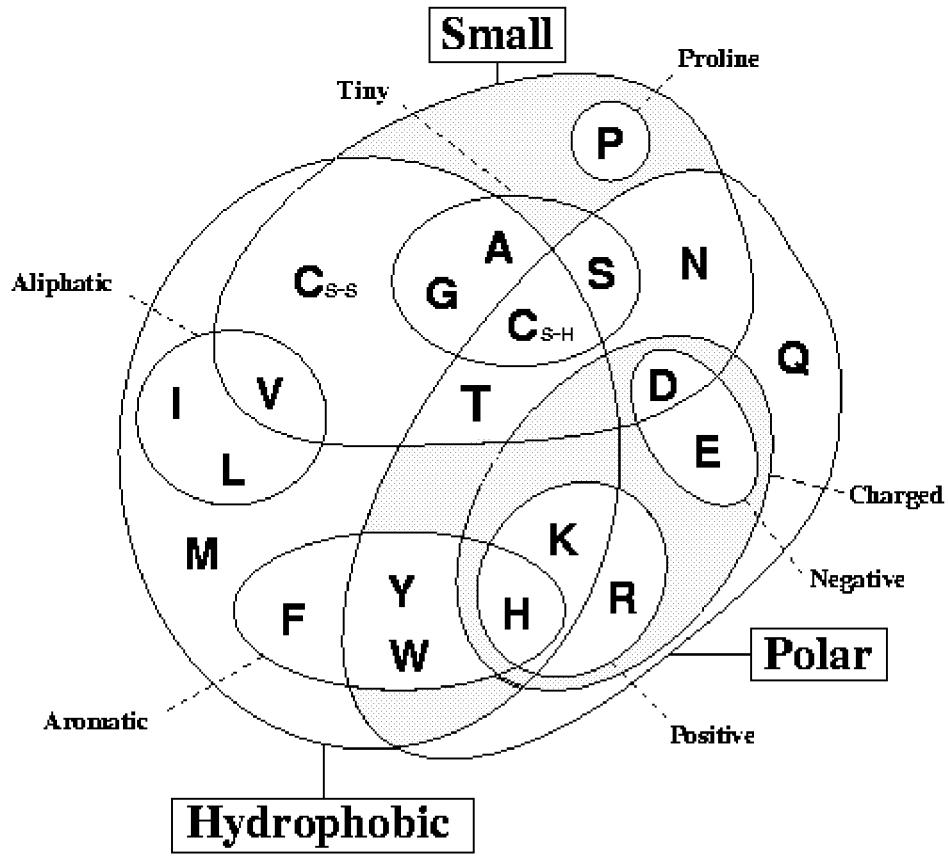
Fig.7: Pharmacokinetics
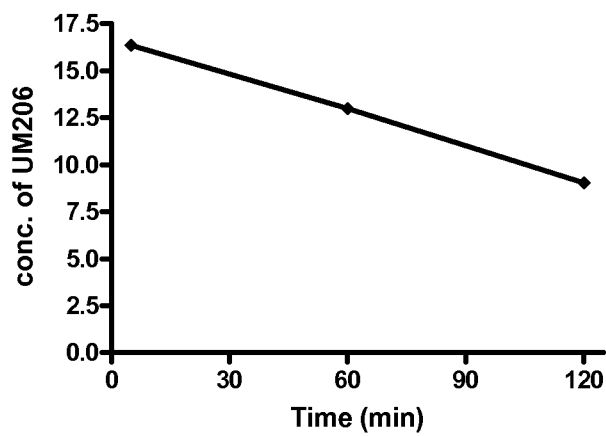

Figure 9A

```
Wnt3a    YFLL----LCSLKQALGSYPIWWSLAVG-----PQYSSLGSQPILCASIPGLVPKQLRFC    56
         +FL+      S  Q +      WWSL +         +G+QP LC+ + GL     Q + C
Wnt5a    FFLMALATFFSFAQVVIEANSWWSLGMNNPVQMSEVHIIGAQP-LCSQLAGLSQGQKKLC    83

Wnt3a    RNYVEIMPSVAEGIKIGIQECQHQFRGRRWNCTTVHDSLAIFGPVLDKATRESAFVHAIA    116
         Y + M   + EG K  GI+ECQ+QFR RRWNC+TV D+ ++FG V+   +RE+AF +A++
Wnt5a    HLYQDHMQYIGEGAKTGIKECQYQFRHRRWNCSTV-DNTSVFGRVMQIGSRETAFTYAVS    142
                       UM207

Wnt3a    SAGVAFAVTRSCAEGTAAICGCS--SRHQGSPGKGWKWGGCSEDIEFGGMVSREFADARE    174
         +AGV A++R+C EG   + CGCS  +R + + P + W WGGC ++I++G   ++EF DARE
Wnt5a    AAGVVNAMSRACREGELSTCGCSRAARPKDLP-RDWLWGGCGDNIDYGYRFAKEFVDARE    201

Wnt3a    NR------PDARSAMNRHNNEAGRQAIASHMHLKCKCHGLSGSCEVKTCWWSQPDFRA    226
         NR        AR  MN HNNEAGR+ + +    + CKCHG+SGSC  +KTCW   DFR
Wnt5a    RERIHAKGSYESARILMNLHNNEAGRRTVYNLADVACKCHGVSGSCSLKTCWLQLADFRK    261
                                                 UM208

Wnt3a    IGDFLKDKYDSASEMVEKHRESRGWVETLRPRYTYFKVPTERDLVYYEASPNFCEPNPE    286
         +GD LK+KYDSA+ M +      SRG + +  R   F  PT +DLVY + SP++C  N
Wnt5a    VGDALKEKYDSAAAMRLN----SRGKLVQVNSR---FNSPTTQDLVYIDPSPDYCVRNES    314

Wnt3a    TGSFGTRDRTCNVSSHGIDGCDLLCCGRGHNARAERRREKCRCVFHWCCYVSCQECTRVY    346
         TGS GT+ R CN +S G+DGC+L+CCGRG++     + E+C C FHWCCYV C++CT +
Wnt5a    TGSLGTQGRLCNKTSEGMDGCELMCCGRGYDQFKTVQTERCHCKFHWCCYVKCKKCTEIV    374
                      UM206

Wnt3a    DVHTCK    352
         D   CK
Wnt5a    DQFVCK    380
```

Figure 9 B, C and D
B.
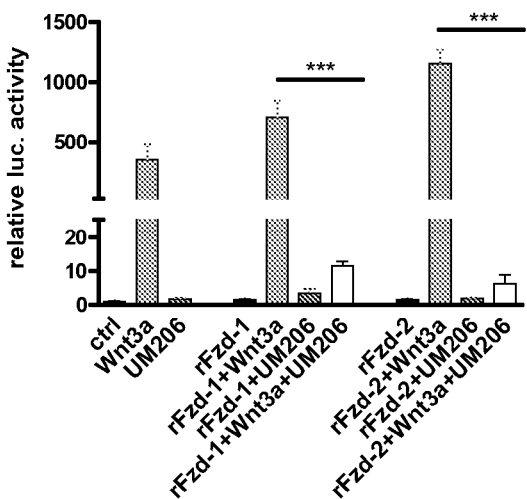
C.
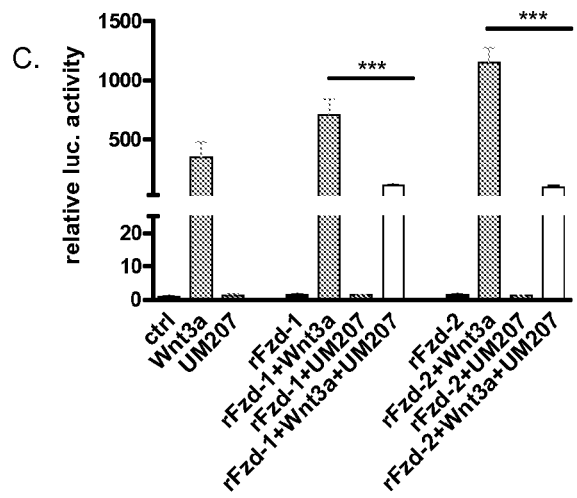
D.
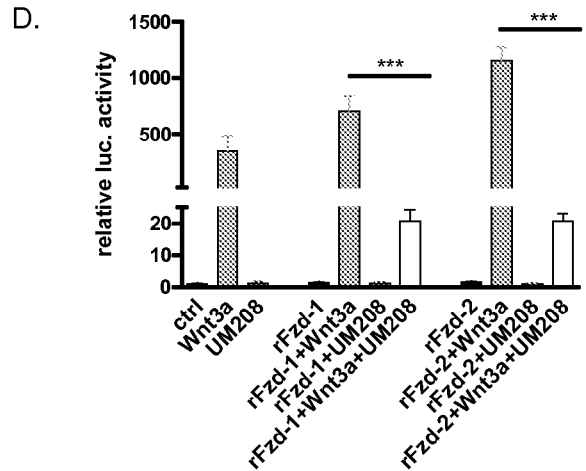

Figure 10
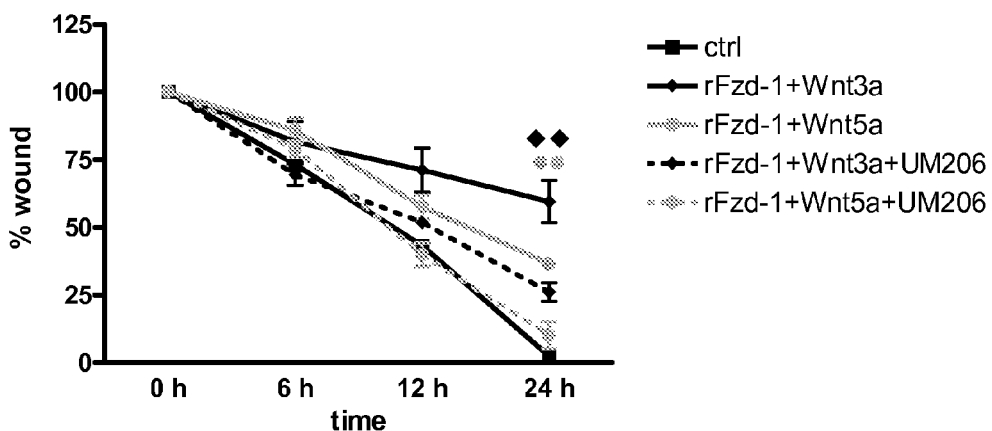
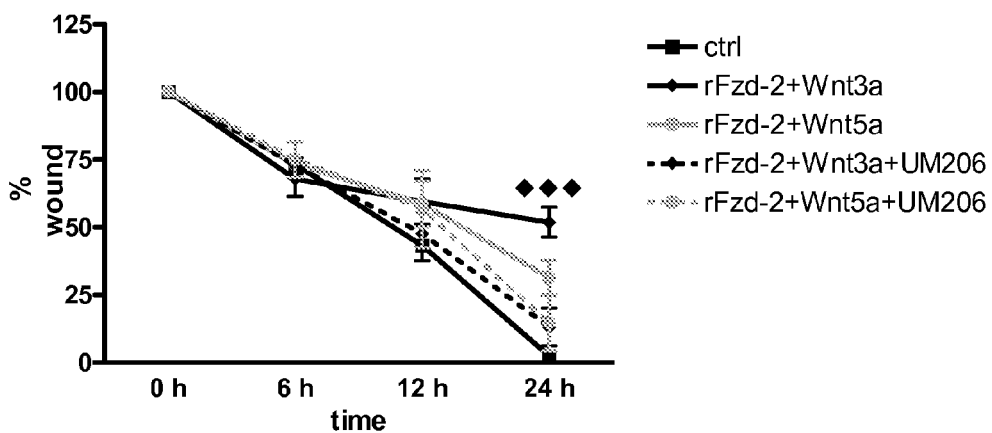

Figure 11
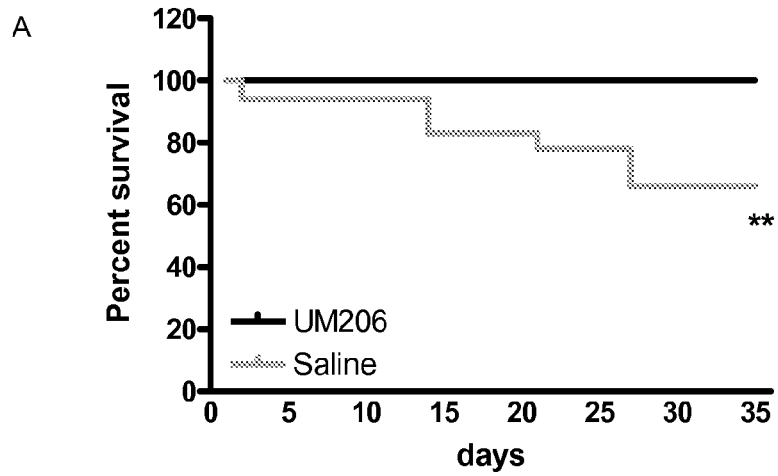
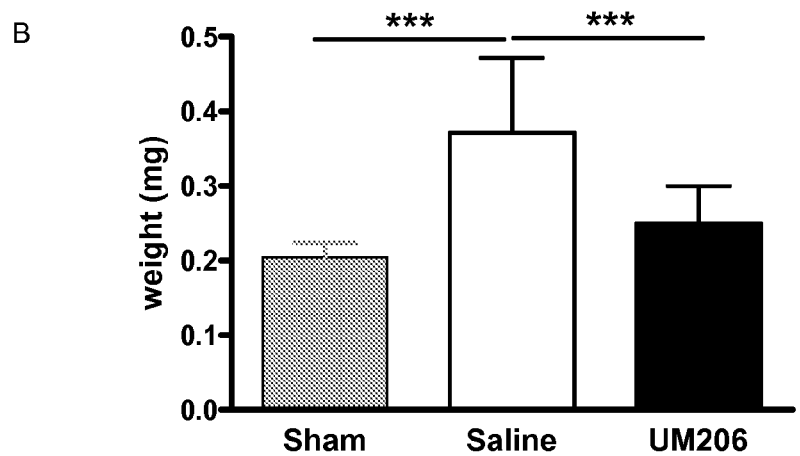
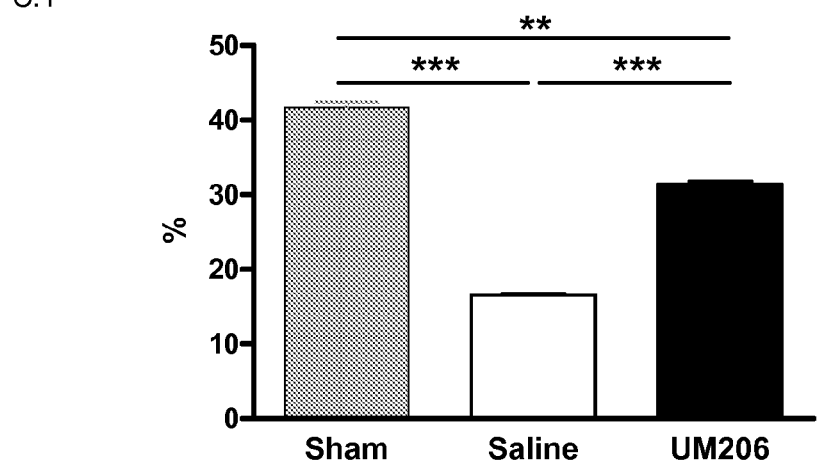

Figure 11 continued
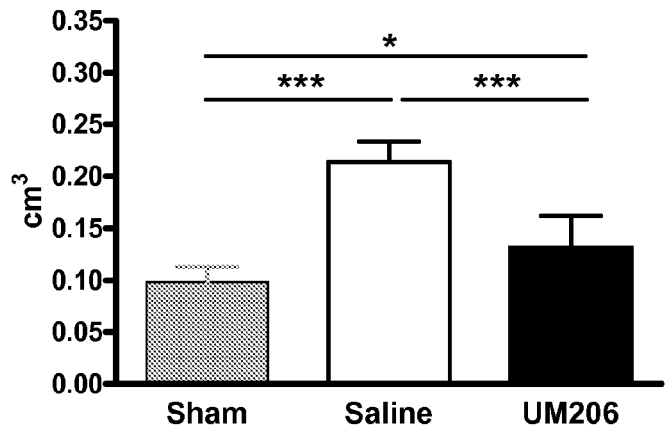
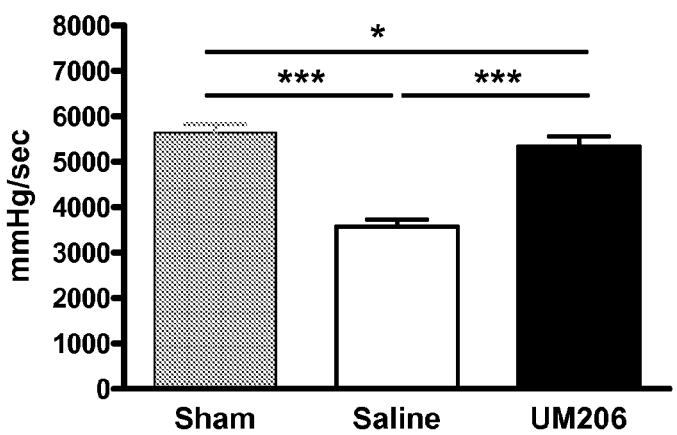
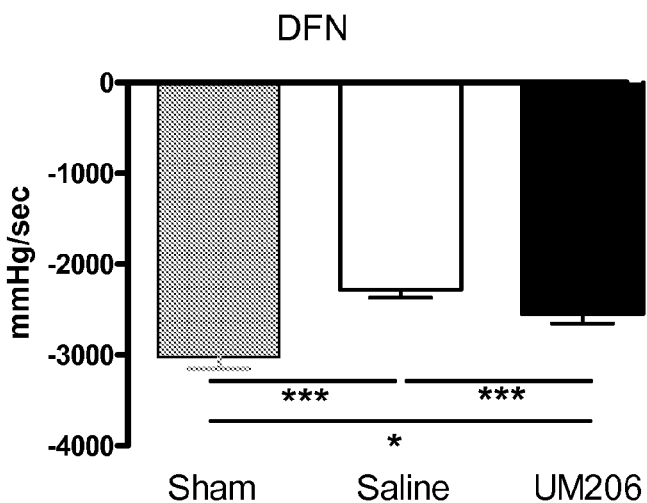

Figure 12
A.1.
UM 206 5 weeks
A.2
Saline 5 weeks

Figure 12 continued
B
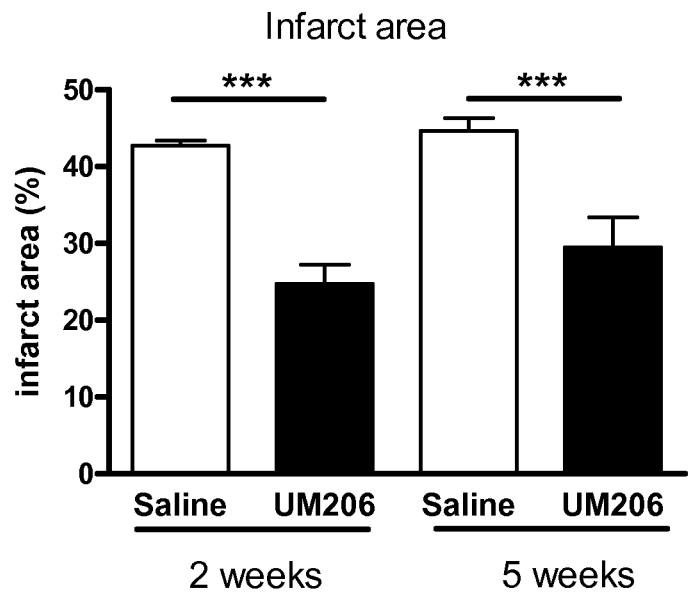
C
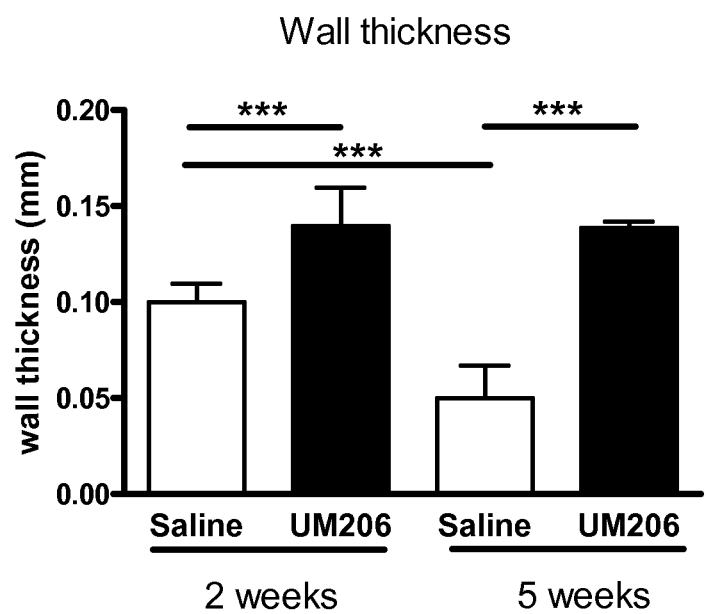

Figure 12 continued
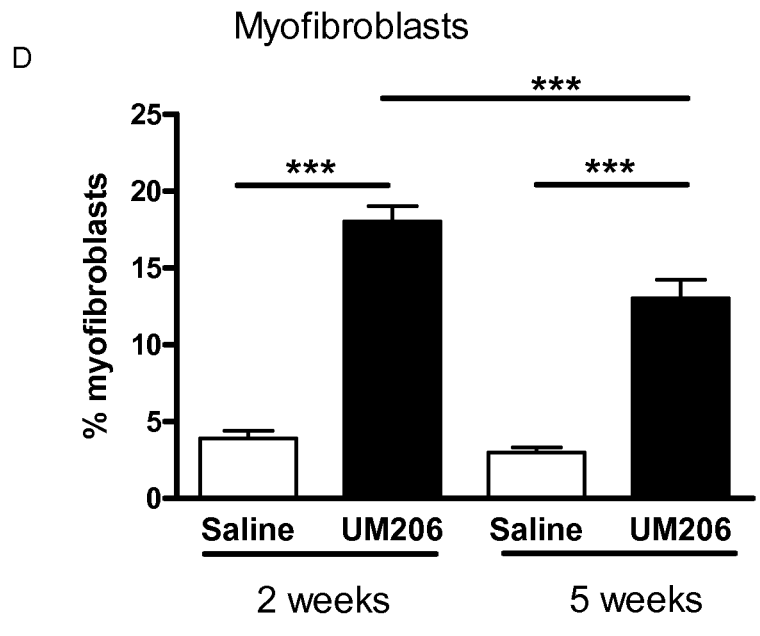
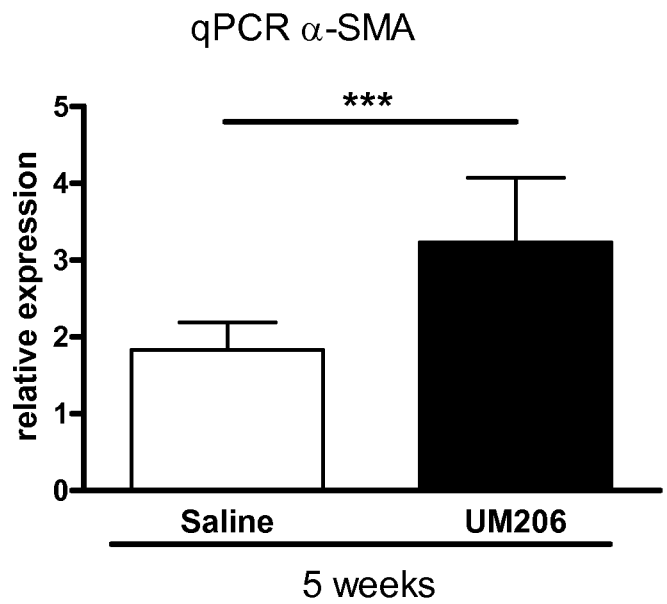

Figure 12 continued
E.2.
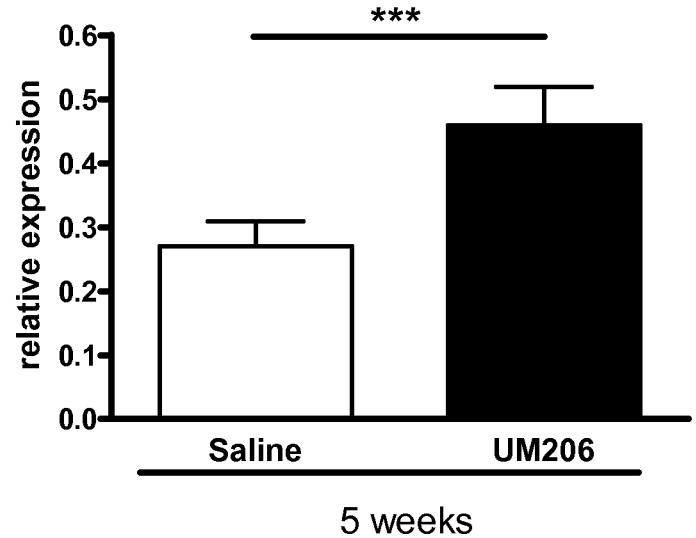
F
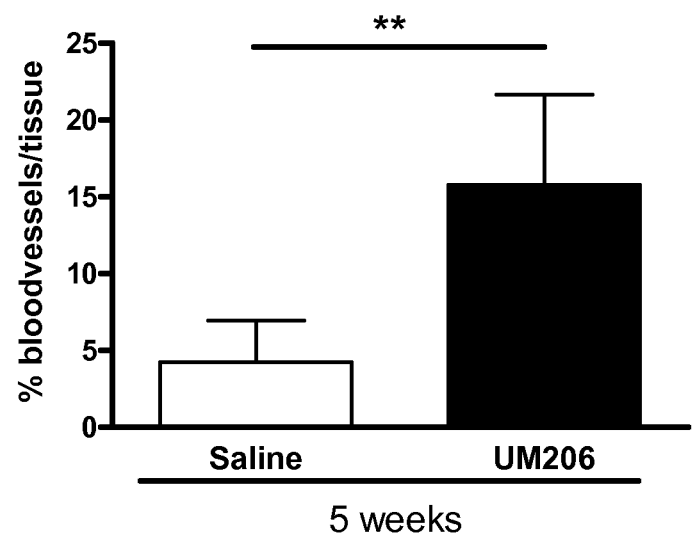

G

Figure 13
A  UM206-Rhodamine
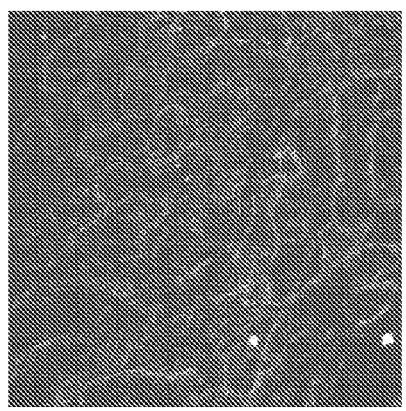 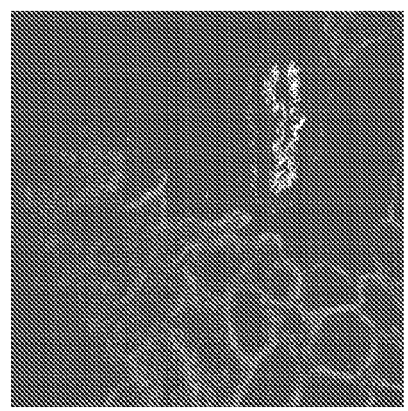
Small intestine       Kidney
B  Pre-incubation UM207
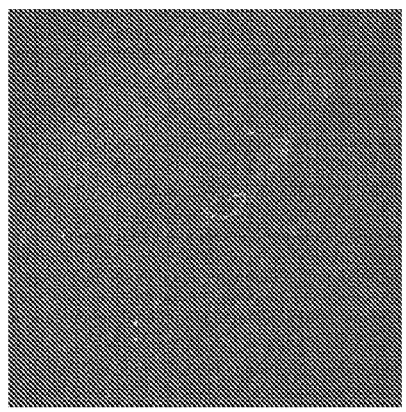 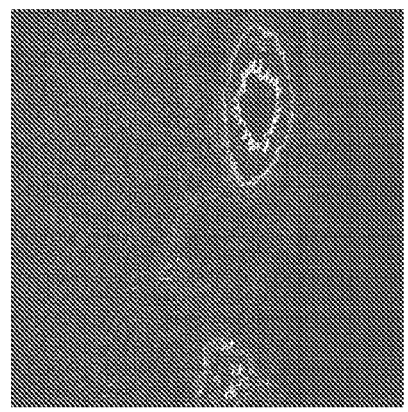
Small intestine       Kidney
C  Pre-incubation rWnt3a
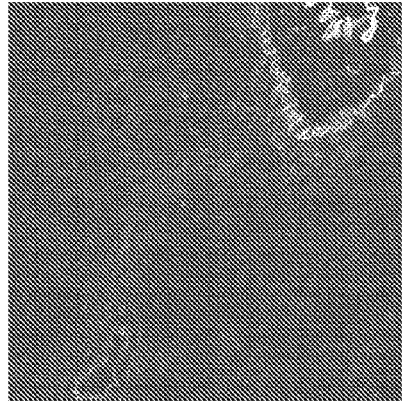 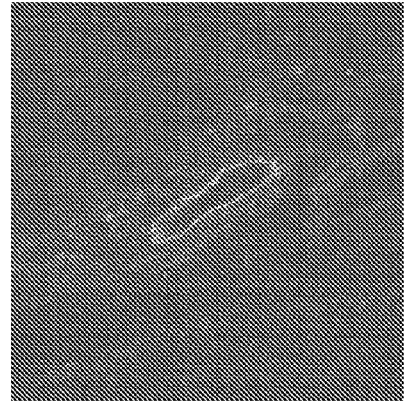
Small intestine       Kidney Figure 14
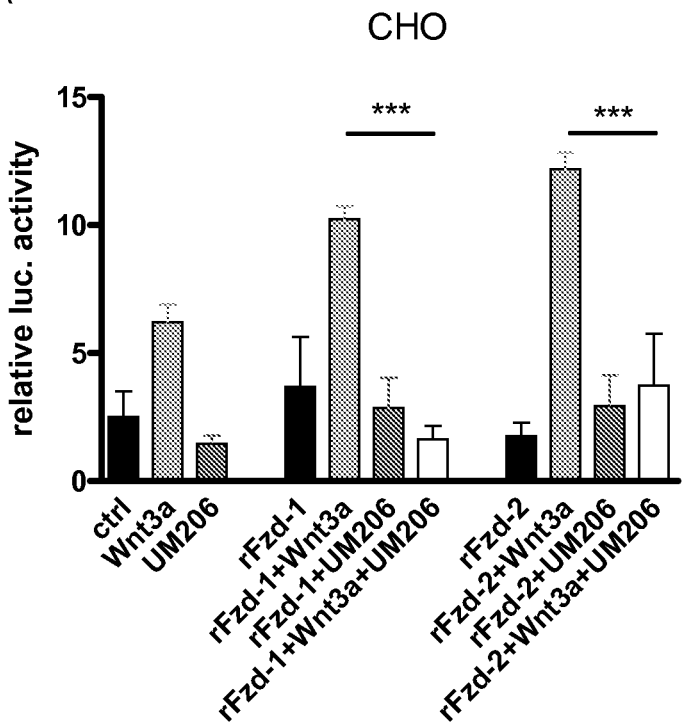
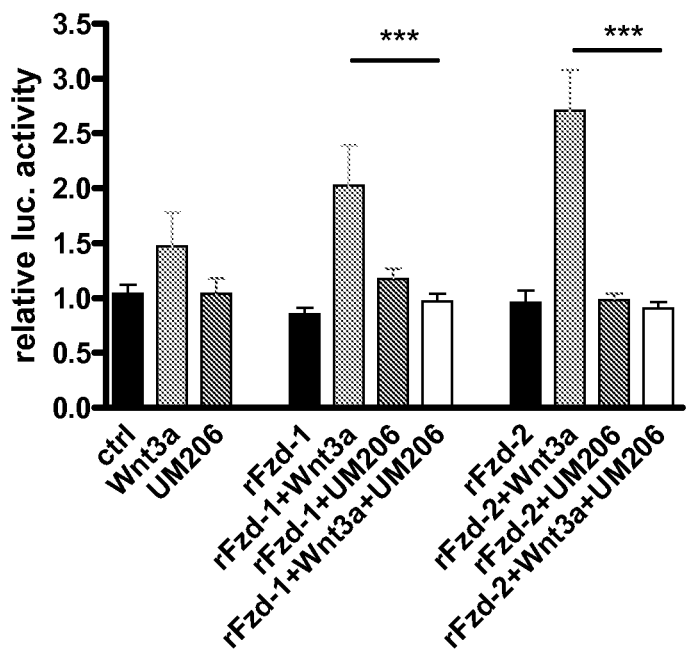

Figure 15
A
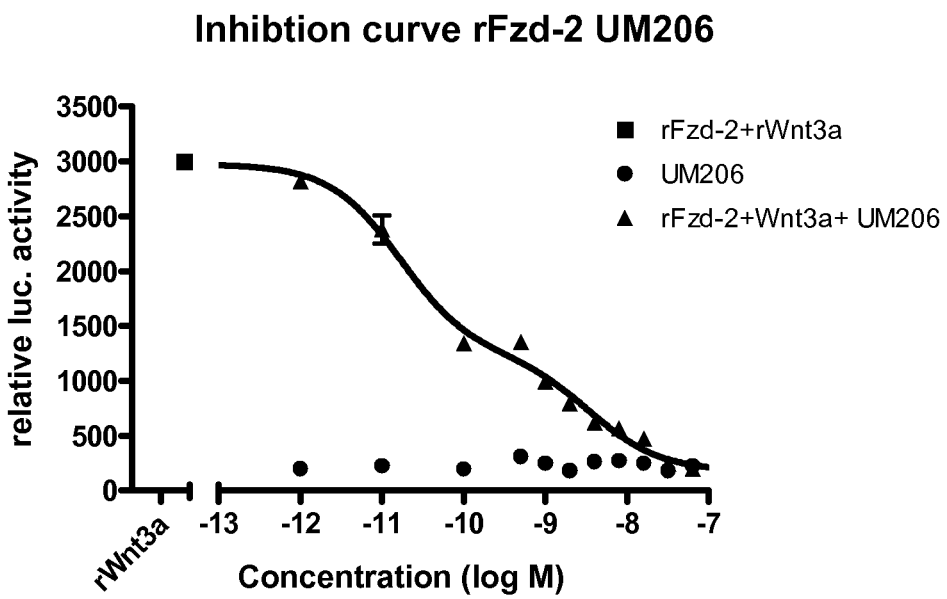
B
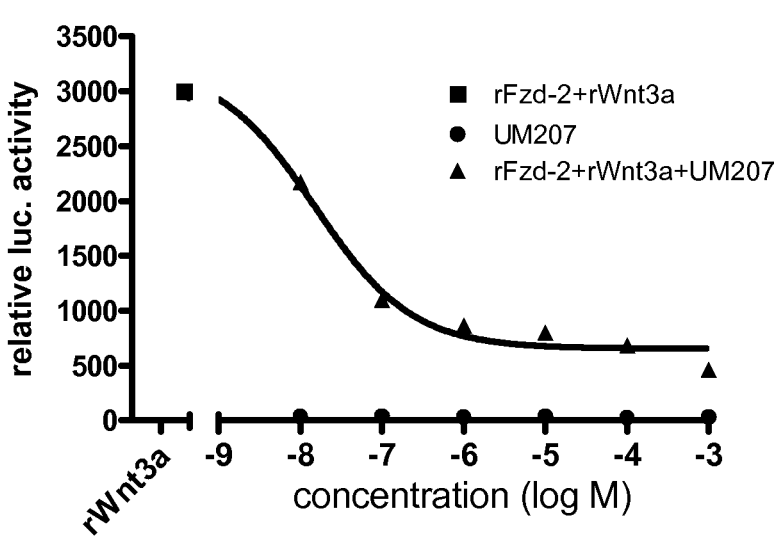

Figure 15 continued
C
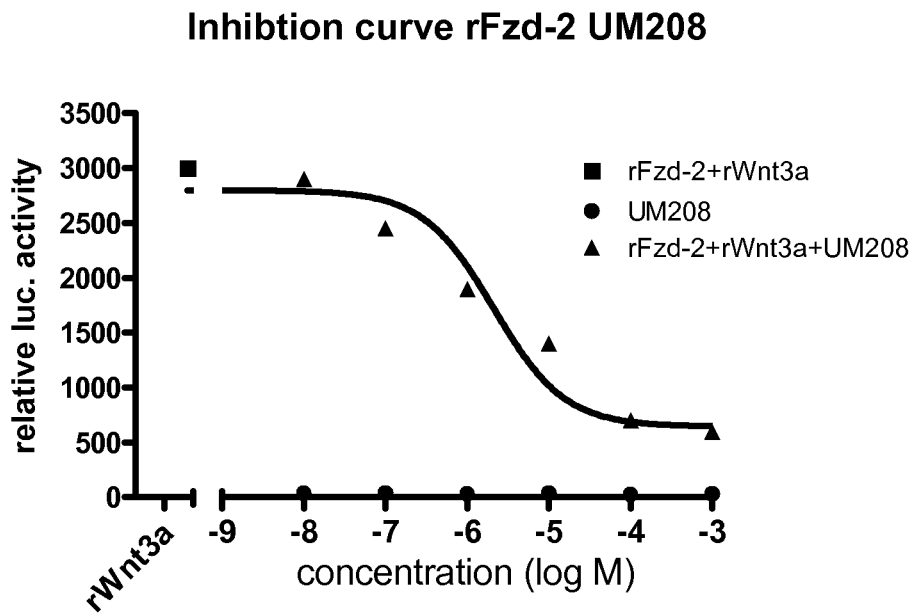
D
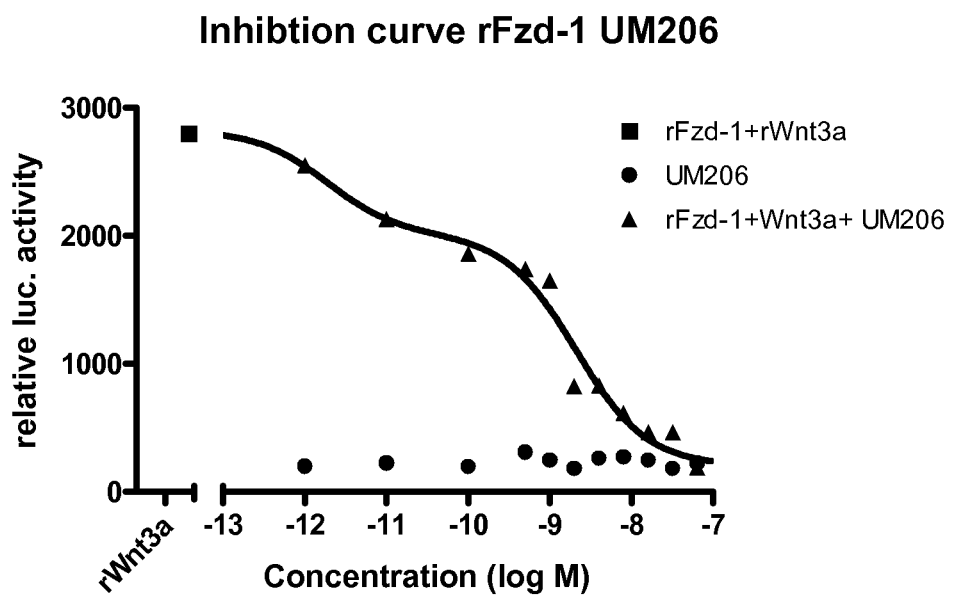

Figure 15 continued
E
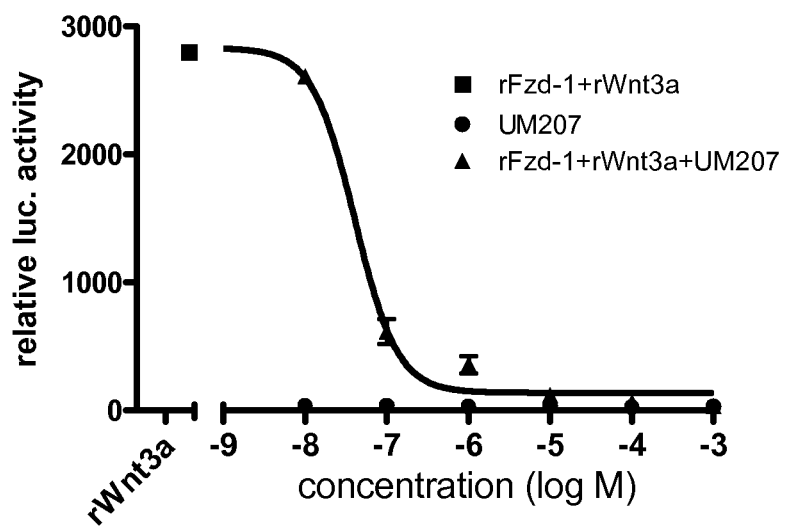
F
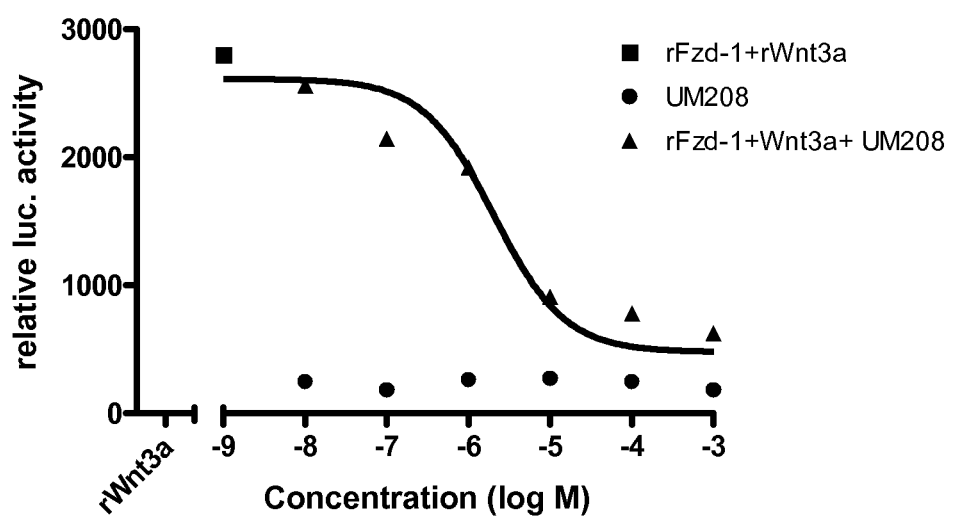

SEQUENCE LISTING

```
<160> NUMBER OF SEQ ID NOS: 23

<210> SEQ ID NO 1
<211> LENGTH: 20
<212> TYPE: PRT
<213> ORGANISM: Homo sapiens

<400> SEQUENCE: 1

Gly Ile Lys Glu Cys Gln Tyr Gln Phe Arg His Arg Arg Trp Asn Cys
1               5                   10                  15

Ser Thr Val Asp
            20

<210> SEQ ID NO 2
<211> LENGTH: 20
<212> TYPE: PRT
<213> ORGANISM: Homo sapiens

<400> SEQUENCE: 2

Gly Ile Gln Glu Cys Gln His Gln Phe Arg Gly Arg Arg Trp Asn Cys
1               5                   10                  15

Thr Thr Ile Asp
            20

<210> SEQ ID NO 3
<211> LENGTH: 20
<212> TYPE: PRT
<213> ORGANISM: Homo sapiens

<400> SEQUENCE: 3

Gly Ile Gln Glu Cys Gln His Gln Phe Arg Gly Arg Arg Trp Asn Cys
1               5                   10                  15

Thr Thr Ile Asp
            20

<210> SEQ ID NO 4
<211> LENGTH: 14
<212> TYPE: PRT
<213> ORGANISM: Homo sapiens

<400> SEQUENCE: 4

Gly Ser Cys Ser Leu Lys Thr Cys Trp Leu Gln Leu Ala Asp
1               5                   10

<210> SEQ ID NO 5
<211> LENGTH: 14
<212> TYPE: PRT
<213> ORGANISM: Homo sapiens

<400> SEQUENCE: 5

Gly Ser Cys Glu Val Lys Thr Cys Trp Trp Ala Gln Pro Asp
1               5                   10
```

```
<210> SEQ ID NO 6
<211> LENGTH: 14
<212> TYPE: PRT
<213> ORGANISM: Homo sapiens

<400> SEQUENCE: 6

Gly Ser Cys Glu Val Lys Thr Cys Trp Trp Ala Gln Pro Asp
1               5                   10

<210> SEQ ID NO 7
<211> LENGTH: 13
<212> TYPE: PRT
<213> ORGANISM: Homo sapiens

<400> SEQUENCE: 7

Cys Asn Lys Thr Ser Glu Gly Met Asp Gly Cys Glu Leu
1               5                   10

<210> SEQ ID NO 8
<211> LENGTH: 13
<212> TYPE: PRT
<213> ORGANISM: Homo sapiens

<400> SEQUENCE: 8

Cys Asn Val Thr Ser His Gly Ile Asp Gly Cys Pro Leu
1               5                   10

<210> SEQ ID NO 9
<211> LENGTH: 13
<212> TYPE: PRT
<213> ORGANISM: Homo sapiens

<400> SEQUENCE: 9

Cys Asn Val Ser Ser His Gly Ile Asp Gly Cys Glu Leu
1               5                   10

<210> SEQ ID NO 10
<211> LENGTH: 16
<212> TYPE: PRT
<213> ORGANISM: Homo sapiens

<400> SEQUENCE: 10

Cys Lys Cys His Gly Val Ser Gly Ser Cys Thr Val Lys Thr Cys Trp
1               5                   10                  15

<210> SEQ ID NO 11
<211> LENGTH: 10
<212> TYPE: PRT
<213> ORGANISM: Homo sapiens

<400> SEQUENCE: 11

Met Asn Arg His Asn Asn Glu Ala Gly Arg
1               5                   10

<210> SEQ ID NO 12
<211> LENGTH: 15
<212> TYPE: PRT
<213> ORGANISM: Homo sapiens

<400> SEQUENCE: 12

Ile Glu Glu Cys Gln His Gln Phe Arg Asp Arg Arg Trp Asn Cys
1               5                   10                  15

<210> SEQ ID NO 13
<211> LENGTH: 12
```

```
<212> TYPE: PRT
<213> ORGANISM: Homo sapiens

<400> SEQUENCE: 13

Gly Asp Trp Glu Trp Gly Glu Cys Ser Asp Asn Ile
1               5                   10

<210> SEQ ID NO 14
<211> LENGTH: 13
<212> TYPE: PRT
<213> ORGANISM: Homo sapiens

<400> SEQUENCE: 14

Asp Leu Val Tyr Phe Glu Leu Ser Pro Asp Phe Cys Ala
1               5                   10

<210> SEQ ID NO 15
<211> LENGTH: 11
<212> TYPE: PRT
<213> ORGANISM: Homo sapiens

<400> SEQUENCE: 15

Gly Ser Lys Gly Thr Gln Gly Arg Ala Cys Asn
1               5                   10

<210> SEQ ID NO 16
<211> LENGTH: 11
<212> TYPE: PRT
<213> ORGANISM: Homo sapiens

<400> SEQUENCE: 16

Cys Asn Lys Ser Gly Met Asp Gly Cys Glu Leu
1               5                   10

<210> SEQ ID NO 17
<211> LENGTH: 20
<212> TYPE: PRT
<213> ORGANISM: Homo sapiens

<400> SEQUENCE: 17

Gly Ile Lys Glu Cys Gln Tyr Gln Phe Arg His Arg Arg Trp Asn Cys
1               5                   10                  15

Ser Thr Val Asp
            20

<210> SEQ ID NO 18
<211> LENGTH: 13
<212> TYPE: PRT
<213> ORGANISM: Homo sapiens

<400> SEQUENCE: 18

Cys Asn Val Ser Ser His Gly Ile Asp Gly Cys Asp Leu
1               5                   10

<210> SEQ ID NO 19
<211> LENGTH: 347
<212> TYPE: PRT
<213> ORGANISM: Homo sapiens

<400> SEQUENCE: 19

Tyr Phe Leu Leu Leu Cys Ser Leu Lys Gln Ala Leu Gly Ser Tyr Pro
1               5                   10                  15

Ile Trp Trp Ser Leu Ala Val Gly Pro Gln Tyr Ser Ser Leu Gly Ser
                20                  25                  30
```

Gln Pro Ile Leu Cys Ala Ser Ile Pro Gly Leu Val Pro Lys Gln Leu
                35                  40                  45

Arg Phe Cys Arg Asn Tyr Val Glu Ile Met Pro Ser Val Ala Glu Gly
 50                  55                  60

Ile Lys Ile Gly Ile Gln Glu Cys Gln His Gln Phe Arg Gly Arg Arg
 65                  70                  75                  80

Trp Asn Cys Thr Thr Val His Asp Ser Leu Ala Ile Phe Gly Pro Val
                85                  90                  95

Leu Asp Lys Ala Thr Arg Glu Ser Ala Phe Val His Ala Ile Ala Ser
                100                 105                 110

Ala Gly Val Ala Phe Ala Val Thr Arg Ser Cys Ala Glu Gly Thr Ala
                115                 120                 125

Ala Ile Cys Gly Cys Ser Ser Arg His Gln Gly Ser Pro Gly Lys Gly
                130                 135                 140

Trp Lys Trp Gly Gly Cys Ser Glu Asp Ile Glu Phe Gly Gly Met Val
145                 150                 155                 160

Ser Arg Glu Phe Ala Asp Ala Arg Glu Asn Arg Pro Asp Ala Arg Ser
                165                 170                 175

Ala Met Asn Arg His Asn Asn Glu Ala Gly Arg Gln Ala Ile Ala Ser
                180                 185                 190

His Met His Leu Lys Cys Lys Cys His Gly Leu Ser Gly Ser Cys Glu
                195                 200                 205

Val Lys Thr Cys Trp Trp Ser Gln Pro Asp Phe Arg Ala Ile Gly Asp
210                 215                 220

Phe Leu Lys Asp Lys Tyr Asp Ser Ala Ser Glu Met Val Val Glu Lys
225                 230                 235                 240

His Arg Glu Ser Arg Gly Trp Val Glu Thr Leu Arg Pro Arg Tyr Thr
                245                 250                 255

Tyr Phe Lys Val Pro Thr Glu Arg Asp Leu Val Tyr Tyr Glu Ala Ser
                260                 265                 270

Pro Asn Phe Cys Glu Pro Asn Pro Glu Thr Gly Ser Phe Gly Thr Arg
                275                 280                 285

Asp Arg Thr Cys Asn Val Ser Ser His Gly Ile Asp Gly Cys Asp Leu
                290                 295                 300

Leu Cys Cys Gly Arg Gly His Asn Ala Arg Ala Glu Arg Arg Arg Glu
305                 310                 315                 320

Lys Cys Arg Cys Val Phe His Trp Cys Cys Tyr Val Ser Cys Gln Glu
                325                 330                 335

Cys Thr Arg Val Tyr Asp Val His Thr Cys Lys
                340                 345

<210> SEQ ID NO 20
<211> LENGTH: 356
<212> TYPE: PRT
<213> ORGANISM: Homo sapiens

<400> SEQUENCE: 20

Phe Phe Leu Met Ala Leu Ala Thr Phe Phe Ser Phe Ala Gln Val Val
1               5                   10                  15

Ile Glu Ala Asn Ser Trp Trp Ser Leu Gly Met Asn Asn Pro Val Gln
                20                  25                  30

Met Ser Glu Val His Ile Ile Gly Ala Gln Pro Leu Cys Ser Gln Leu
                35                  40                  45

Ala Gly Leu Ser Gln Gly Gln Lys Lys Leu Cys His Leu Tyr Gln Asp
                50                  55                  60

```
His Met Gln Tyr Ile Gly Glu Gly Ala Lys Thr Gly Ile Lys Glu Cys
 65                  70                  75                  80

Gln Tyr Gln Phe Arg His Arg Arg Trp Asn Cys Ser Thr Val Asp Asn
                 85                  90                  95

Thr Ser Val Phe Gly Arg Val Met Gln Ile Gly Ser Arg Glu Thr Ala
            100                 105                 110

Phe Thr Tyr Ala Val Ser Ala Ala Gly Val Val Asn Ala Met Ser Arg
        115                 120                 125

Ala Cys Arg Glu Gly Glu Leu Ser Thr Cys Gly Cys Ser Arg Ala Ala
130                 135                 140

Arg Pro Lys Asp Leu Pro Arg Asp Trp Leu Trp Gly Gly Cys Gly Asp
145                 150                 155                 160

Asn Ile Asp Tyr Gly Tyr Arg Phe Ala Lys Glu Phe Val Asp Ala Arg
                165                 170                 175

Glu Arg Glu Arg Ile His Ala Lys Gly Ser Tyr Glu Ser Ala Arg Ile
            180                 185                 190

Leu Met Asn Leu His Asn Asn Glu Ala Gly Arg Arg Thr Val Tyr Asn
        195                 200                 205

Leu Ala Asp Val Ala Cys Lys Cys His Gly Val Ser Gly Ser Cys Ser
210                 215                 220

Leu Lys Thr Cys Trp Leu Gln Leu Ala Asp Phe Arg Lys Val Gly Asp
225                 230                 235                 240

Ala Leu Lys Glu Lys Tyr Asp Ser Ala Ala Met Arg Leu Asn Ser
                245                 250                 255

Arg Gly Lys Leu Val Gln Val Asn Ser Arg Phe Asn Ser Pro Thr Thr
            260                 265                 270

Gln Asp Leu Val Tyr Ile Asp Pro Ser Pro Asp Tyr Cys Val Arg Asn
        275                 280                 285

Glu Ser Thr Gly Ser Leu Gly Thr Gln Gly Arg Leu Cys Asn Lys Thr
290                 295                 300

Ser Glu Gly Met Asp Gly Cys Glu Leu Met Cys Cys Gly Arg Gly Tyr
305                 310                 315                 320

Asp Gln Phe Lys Thr Val Gln Thr Glu Arg Cys His Cys Lys Phe His
                325                 330                 335

Trp Cys Cys Tyr Val Lys Cys Lys Lys Cys Thr Glu Ile Val Asp Gln
            340                 345                 350

Phe Val Cys Lys
        355

<210> SEQ ID NO 21
<211> LENGTH: 55
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Positions 1 and/or 45 are Cys
<220> FEATURE:
<221> NAME/KEY: MISC_FEATURE
<222> LOCATION: (2)..(11)
<223> OTHER INFORMATION: Positions 2 to 11 can include up to 10 amino
      acids; or, these amino acids may be missing
<220> FEATURE:
<221> NAME/KEY: MISC_FEATURE
<222> LOCATION: (13)..(22)
<223> OTHER INFORMATION: Positions 13 to 22 can include up to 10 amino
      acids; or, these amino acids may be missing
<220> FEATURE:
<221> NAME/KEY: MISC_FEATURE
<222> LOCATION: (24)..(3)
<223> OTHER INFORMATION: Positions 24 to 33 can include up to 10 amino
```

```
       acids; or, these amino acids may be missing
<220> FEATURE:
<221> NAME/KEY: misc_feature
<222> LOCATION: (24)..(33)
<223> OTHER INFORMATION: Xaa can be any naturally occurring amino acid
<220> FEATURE:
<221> NAME/KEY: MISC_FEATURE
<222> LOCATION: (35)..(44)
<223> OTHER INFORMATION: Positions 35 to 44 can include up to 10 amino
       acids; or, these amino acids may be missing
<220> FEATURE:
<221> NAME/KEY: MISC_FEATURE
<222> LOCATION: (45)..(45)
<223> OTHER INFORMATION: Positions 1 and/or 45 are Cys
<220> FEATURE:
<221> NAME/KEY: MISC_FEATURE
<222> LOCATION: (46)..(55)
<223> OTHER INFORMATION: Positions 46 to 55 can include up to 10 amino
       acids; or, these amino acids may be missing

<400> SEQUENCE: 21

Xaa Xaa Xaa Xaa Xaa Xaa Xaa Xaa Xaa Xaa Xaa Thr Xaa Xaa Xaa Xaa
1               5                   10                  15

Xaa Xaa Xaa Xaa Xaa Xaa Gly Xaa Xaa Xaa Xaa Xaa Xaa Xaa Xaa
            20                  25                  30

Xaa Asp Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa
    50                  55

<210> SEQ ID NO 22
<211> LENGTH: 65
<212> TYPE: PRT
<213> ORGANISM: Homo sapiens
<220> FEATURE:
<221> NAME/KEY: MISC_FEATURE
<222> LOCATION: (2)..(11)
<223> OTHER INFORMATION: Positions 2 to 11 can include up to 10 amino
       acids; or, these amino acids may be missing
<220> FEATURE:
<221> NAME/KEY: MISC_FEATURE
<222> LOCATION: (12)..(12)
<223> OTHER INFORMATION: Positions 12 and/or 33 are Cys
<220> FEATURE:
<221> NAME/KEY: MISC_FEATURE
<222> LOCATION: (13)..(17)
<223> OTHER INFORMATION: Positions 13 to 37 may be any amino acid
<220> FEATURE:
<221> NAME/KEY: MISC_FEATURE
<222> LOCATION: (18)..(32)
<223> OTHER INFORMATION: Positions 18 to 32 can include up to 15
       amino acids; or, these amino acids may be missing
<220> FEATURE:
<221> NAME/KEY: MISC_FEATURE
<222> LOCATION: (33)..(33)
<223> OTHER INFORMATION: Positions 12 and/or 33 are Cys
<220> FEATURE:
<221> NAME/KEY: MISC_FEATURE
<222> LOCATION: (34)..(43)
<223> OTHER INFORMATION: Positions 34 to 43 can include up to 10 amino
       acids; or, these amino acids may be missing
<220> FEATURE:
<221> NAME/KEY: MISC_FEATURE
<222> LOCATION: (45)..(54)
<223> OTHER INFORMATION: Positions 45 to 54 can include up to 10 amino
       acids; or, these amino acids may be missing
<220> FEATURE:
<221> NAME/KEY: MISC_FEATURE
<222> LOCATION: (56)..(65)
<223> OTHER INFORMATION: Positions 56 to 65 can include up to 10 amino
       acids; or, these amino acids may be missing

<400> SEQUENCE: 22

Gly Xaa Xaa Xaa Xaa Xaa Xaa Xaa Xaa Xaa Xaa Xaa Xaa Xaa Xaa Xaa
```

```
                1               5              10              15
Xaa Xaa Xaa Xaa Xaa Xaa Xaa Xaa Xaa Xaa Xaa Xaa Xaa Xaa Xaa
              20              25              30
Xaa Xaa Xaa Xaa Xaa Xaa Xaa Xaa Xaa Xaa Xaa Thr Xaa Xaa Xaa Xaa
              35              40              45
Xaa Xaa Xaa Xaa Xaa Xaa Asp Xaa Xaa Xaa Xaa Xaa Xaa Xaa Xaa
              50              55              60
Xaa
65

<210> SEQ ID NO 23
<211> LENGTH: 56
<212> TYPE: PRT
<213> ORGANISM: Homo sapiens
<220> FEATURE:
<221> NAME/KEY: MISC_FEATURE
<222> LOCATION: (2)..(11)
<223> OTHER INFORMATION: Positions 2 to 11 can include up to 10 amino
      acids; or, these amino acids may be missing
<220> FEATURE:
<221> NAME/KEY: MISC_FEATURE
<222> LOCATION: (11)..(11)
<223> OTHER INFORMATION: Position 11 is a tail of 0 to 10 amino acids
<220> FEATURE:
<221> NAME/KEY: MISC_FEATURE
<222> LOCATION: (12)..(12)
<223> OTHER INFORMATION: Positions 12 and/or 24 are Cys
<220> FEATURE:
<221> NAME/KEY: MISC_FEATURE
<222> LOCATION: (13)..(22)
<223> OTHER INFORMATION: Positions 13 to 22 can include up to 10 amino
      acids; or, these amino acids may be missing
<220> FEATURE:
<221> NAME/KEY: MISC_FEATURE
<222> LOCATION: (24)..(24)
<223> OTHER INFORMATION: Positions 12 and/or 24 are Cys
<220> FEATURE:
<221> NAME/KEY: MISC_FEATURE
<222> LOCATION: (24)..(34)
<223> OTHER INFORMATION: Positions 25 to 34 can include up to 10 amino
      acids; or, these amino acids may be missing
<220> FEATURE:
<221> NAME/KEY: MISC_FEATURE
<222> LOCATION: (36)..(45)
<223> OTHER INFORMATION: Positions 36 to 45 can include up to 10 amino
      acids; or, these amino acids may be missing
<220> FEATURE:
<221> NAME/KEY: MISC_FEATURE
<222> LOCATION: (47)..(56)
<223> OTHER INFORMATION: Positions 47 to 56 can include up to 10 amino
      acids; or, these amino acids may be missing

<400> SEQUENCE: 23

Gly Xaa Xaa Xaa Xaa Xaa Xaa Xaa Xaa Xaa Xaa Xaa Xaa Xaa Xaa
1               5              10              15
Xaa Xaa Xaa Xaa Xaa Xaa Gly Xaa Xaa Xaa Xaa Xaa Xaa Xaa Xaa
              20              25              30
Xaa Xaa Thr Xaa Xaa Xaa Xaa Xaa Xaa Xaa Xaa Xaa Asp Xaa Xaa
              35              40              45
Xaa Xaa Xaa Xaa Xaa Xaa Xaa Xaa
              50              55
```

ANTAGONISTIC PEPTIDES FOR FRIZZLED-1 AND FRIZZLED-2

CROSS-REFERENCE TO RELATED APPLICATIONS

This is a national phase entry under 35 U.S.C. §371 of International Patent Application PCT/EP2010/052058, filed Feb. 18, 2010, published in English as International Patent Publication WO 2010/100035 A1on Sep. 10, 2010, which claims the benefit under Article 8 of the Patent Cooperation Treaty to European Patent Application Serial No. 09154475.9, filed Mar. 5, 2009.

TECHNICAL FIELD

The invention is in the field of molecular medicine. It provides antagonistic compounds for frizzled-1 and/or frizzled-2 receptors, which may be useful in molecular imaging of the wound healing process after myocardial infarction and in therapeutic intervention into wound healing after remodeling of the heart, thereby ameliorating the consequences of myocardial infarction.

BACKGROUND

The frizzled receptor is a seven-transmembrane receptor belonging to the family of G-coupled receptors, with a long extracellular domain. This extracellular part has a cysteine-rich domain, called the CRD, which defines the binding region for the natural ligands, the so-called Wnt proteins. The intracellular part enables the prolongation of the signal. A schematic representation of the structure of frizzled receptors is shown in FIG. 1.

There are ten different frizzled receptors that slightly differ in the variable cytoplasmatic part and the Wnt binding domain. When an agonistic ligand binds to the receptor, a signal transduction cascade gets activated. The Wnt/frizzled signaling can be subdivided in three pathways: first, the canonical pathway or beta-catenin-dependent pathway with second messenger β-catenin; second, the a-specific or beta-catenin-independent pathway formerly known as non-canonical pathway via calcium; and third, the planar cell polarity pathway.

There are 19 different Wnt proteins that can be subdivided into two families, namely, the Wnt1 class, inducing secondary axis via the canonical pathway and the Wnt5a class working via the second messenger calcium, without inducing secondary axis.

Wnt proteins are very large proteins that tend to stick to the extracellular matrix and other biological and non-biological substances in a non-specific way. Because of its lack of specific binding, the natural ligand of the frizzled receptor is not suitable for visualization of the receptor. Native Wnt proteins may be experimentally used, however, for the induction of the Wnt signaling pathway through interaction with a frizzled receptor.

Many developmental diseases and diseases linked with a reactivation of the embryonic gene program are associated with re-expression of the Wnt/frizzled signal transduction cascade. The Wnt/frizzled pathway provides screening possibilities, not only for wound healing in the heart, but also for osteo-arthritis and rheumatic arthritis. Main differences between these two are based on the presence or absence of the frizzled receptor. Specific frizzled binding peptides may, therefore, differentiate between the two and make more specific and appropriate treatment of these patients possible.

Furthermore, diseases as idiopathic pulmonary disease, liver disease and renal fibrosis, are associated with the Wnt/frizzled pathway. All these diseases give rise to a reactivation of the embryonic gene program, therefore, activation of the Wnt/frizzled signal transduction cascade. This reactivation will lead to fibrosis and, therefore, organ malfunctioning.

Proteins from the Wnt family have been implicated in cell—cell communication in a wide variety of developmental and physiological processes. Wnt signaling is required for different aspects of cardiac and vascular development, including myocardial specification, cardiac morphogenesis and cardiac valve formation, as well as endothelial and vascular smooth muscle cell proliferation. Defective Wnt signaling can result in different cardiac and vascular abnormalities.

In the adult heart and blood vessels, Wnt signaling activity is quite low under normal conditions. However, this pathway is reactivated during the pathological remodeling induced by pressure overload, in injured arteries and after myocardial infarction.

Myocardial infarction (MI) is characterized by the death of cells in the heart due to occlusion of a coronary artery, which supplies blood to the heart. Some people will have a relatively good functioning heart after MI, whereas others have dilated hearts, which function very badly.

It has been described that the well-healed heart contains more myofibroblasts in the infarcted area. Further research has shown that these hearts have increased levels of frizzled-1 and, especially, frizzled-2; whereas these receptors were mainly present on newly formed myofibroblasts. It has been proposed that these myofibroblasts give the heart the ability to preserve some of its geometry and structure.

Genetically modified animal models have shown that inhibition of Wnt signaling results in increased angiogenesis, better infarct healing and an attenuated hypertrophic response of the heart. This suggests that pharmacological inhibition of Wnt signaling could provide a good therapeutic strategy to prevent excessive cardiac and vascular remodeling (van de Schans et al., *Eur. J. Pharmacol.* 585:338-345 (2008)).

Antagonist of the Wnt/frizzled pathway may, therefore, prevent fibrosis and prevent malfunctioning of vital organs as the heart (Blankesteijn et al., 1996; van de Schans et al., 2008), lungs (Konigshoff et al., 2008), kidney (Surendran et al., 2002) and liver (Thompson and Monga, 2007). Antagonists of the Wnt/frizzled pathway may also be useful in the treatment of injured skeletal muscles, which could be better healed after inhibiting the Wnt/frizzled signal transduction. Aging may also be slowed down by inhibition of the Wnt/Fz signal transduction cascade. (Brack et al., 2007; Imai et al., 2006; Konigshoff et al., 2008; Li et al., 2004; Surendran et al., 2002; Thompson and Monga, 2007.)

Unfortunately, no antagonists for the frizzled receptors have been described to date. Therefore, until now, the only way to intervene in the Wnt/frizzled pathway is at the level of the second messenger or other downstream signal elements, leading to aspecific blocking and interference in other signaling transduction cascades.

To limit the influences on other biological processes, it would be desirable to intervene on the receptor-ligand level by providing antagonists for the frizzled receptor.

DISCLOSURE

We have found that the interaction between Wnt and frizzled-1 and/or frizzled-2 may be blocked by occupying the receptor with a ligand derived from Wnt3, Wnt3a or Wnt5a. Such a ligand may be obtained by rational design including 1) the selection of highly homologous regions between Wnt3a, Wnt3 and Wnt5a, 2) selection of regions ranging from 13 to 22 amino acids that contain at least two cysteines, 3) exclusion of region 1 to 77 of the Wnt5a sequence or corresponding regions in the other Wnt proteins that are necessary for excretion or post-translational modification of Wnt3, Wnt3a and Wnt5a. Such a ligand provides a specific interaction with one type of receptor and can, therefore, be used as a therapeutic tool for Wnt/frizzled-related diseases. These molecules may also be used as an imaging tool in the further research towards the interaction between Wnt and frizzled receptors.

The invention, therefore, provides a method for antagonizing frizzled-1 or frizzled-2 receptors, wherein the receptor is contacted with a composition comprising a linear fragment of Wnt3, Wnt3a or Wnt5a or a functional analogue thereof The preferred fragments all comprised a set of essential amino acid residues. The invention, therefore, relates to fragments that comprise at least one cysteine residue, one threonine residue, one aspartic acid residue and one glycine residue. The invention also provides a method for visualizing the frizzled receptor, wherein a preparation comprising a frizzled receptor is contacted with a composition comprising a linear fragment of Wnt3, Wnt3a or Wnt5a or a functional analogue thereof, which comprises at least one cysteine residue, one threonine residue, one aspartic acid residue and one glycine residue.

We have found that a linear fragment of Wnt3, Wnt3a or Wnt5a proteins was capable of antagonizing frizzled receptors. We have identified the critical amino acids of such fragments and were able to show that the linear peptides as identified herein are capable of inducing effects in vitro as well as in vivo.

We have also found that one and the same primary amino acid sequence can act as an antagonist or agonist, depending on its linear or cyclic conformation. Fragments derived from Wnt3 and/or from Wnt3a and/or from Wnt5a acted as an antagonist when in the linear state, the same fragments were effective agonists when in the cyclic conformation.

It was found that such peptides need to contain at least one cysteine residue for efficient antagonistic activity. They may also contain two cysteine residues as long as it is prevented that the cysteines form a cyclic bond, for instance, through S-S bridging. The oxidation of the dithiol appears to be difficult to achieve as a consequence of steric hindering and its formation needs well-determined circumstances. At a physiological pH of 7.4 and normal oxygen levels at 37° C., the peptide fragments with two cysteine residues were unable to form the disulfide bond, even after 48 hours. An elevated oxygen concentration, adapted pH and sufficient time were necessary to form the disulfide bond, therefore, the disulfide bond cannot be reached naturally.

The peptide sequence may preferably be selected from the homologous regions of the natural ligands for frizzled-1 or frizzled 2, namely, Wnt3, Wnt3a or Wnt5a. Example peptides selected from these regions are listed in Table 1.

TABLE 1

| Peptide | Fragment aa#-aa# | Sequence | SEQ ID NO: |
|---|---|---|---|
| Wnt5a | 99-119 | GIKECQYQFRHRRWNCSTVD | 1 |
| Wnt3 | 71-90 | GIQECQHQFRGRRWNCTTID | 2 |
| Wnt3a | 74-93 | GIQECQHQFRGRRWNCTTID | 3 |
| Wnt5a | 244-258 | GSCSLKTCWLQLAD | 4 |

TABLE 1-continued

| Peptide | Fragment aa#-aa# | Sequence | SEQ ID NO: |
|---|---|---|---|
| Wnt3 | 212-223 | GSCEVKTCWWAQPD | 5 |
| Wnt3a | 215-226 | GSCEVKTCWWAQPD | 6 |
| Wnt5a | 324-335 | CNKTSEGMDGCEL | 7 |
| Wnt3 | 296-307 | CNVTSHGIDGCPL | 8 |
| Wnt3a | 299-310 | CNVSSHGIDGCEL | 9 |

Homologous regions are herein defined as regions that have a homology of more than 50%, such as 58% or more, such as 61% or more, such as 77% or more, or even 80%, 90%, 92%, 94%, 96%, 98% or even 100%. Calculation of the homology of a certain region is a standard procedure for the skilled person. Guidance for determining the homology of two regions of a nucleic acid can be found in Sambrook et al., *Molecular Cloning: A Laboratory Manual* (Third Edition).

Peptide UM206 was derived from the primary sequence of Wnt3, Wnt3a and Wnt5a (amino acids 296 through 307 and 324 through 335, respectively). UM206 has the primary sequence as follows:

Peptide UM206:

(SEQ ID NO: 7)
Ac-Cys-Asn-Lys-Thr-Ser-Glu-Gly-Met-Asp-Gly-Cys-Glu-Leu-NH$_2$

The peptide was found to be in a linear conformation under physiological conditions. When forced into a cyclic state by inducing the formation of a disulfide bridge between the two cysteine residues, the following peptide was obtained.

Peptide UM206(S-S);

(SEQ ID NO: 7)

Ac-Cys-Asn-Lys-Thr-Ser-Glu-Gly-Met-Asp-Gly-Cys-Glu-Leu-NH$_2$

When these peptides were tested for activity on the frizzled receptor in our experimental model as described in Example 1, it was found that the peptide without the sulphur bridge (peptide UM206) acted as a very potent antagonist, whereas the oxidized peptide containing the sulphur bridge acted as a potent agonist.

The results of the experiments are shown in FIG. 3. This figure shows a twelve-fold concentration-dependent increase of the luciferase activity for the natural ligand Wnt3a in combination with frizzled-2 (●) and this is completely and concentration-dependently blocked with increasing amounts of antagonist UM206 (□). The antagonist on its own has no effect (■). The IC50 value (concentration of antagonist at which 50% of the activity of the natural ligand is inhibited) is $10^{-10}$ M (see FIG. 3, Panel A). When the antagonist was tested against frizzled-1, the IC50 value was found to be $10^{-9}$ M (see FIG. 3, Panel C).

Next, the agonist (UM206 S-S) was tested for activity against the frizzled-1 and frizzled-2 receptors. For that purpose, the cells were transfected with either Fz1 or Fz2 and the agonist was added in increasing amounts. The same test system as described in Example 1 was used, and the EC$_{50}$ (amount of agonist that yields 50% of maximum activity) was measured. The EC50 for frizzled-2 was $2.10^{-8}$ M and for frizzled-1 $10^{-8}$. (See FIG. 3, Panels D and B.)

Table 3 shows a number of alternative peptides that were tested, but were unable to influence the Wnt/Fzd signal transduction cascade. The sequences of these peptides do not comply with the above-described criteria for Fzd ligands.

TABLE 3

|  | Sequence | SEQ ID NO: |
|---|---|---|
| Peptide 1 | Ac-CKCHGVSGSCTVKTCW-NH$_2$ | 10 |
| Peptide 2 | Ac-MNRHNNEAGR-NH$_2$ | 11 |
| Peptide 3 | Ac-IEECQHQFRDRRWNC-NH$_2$ | 12 |
| Peptide 4 | Ac-GDWEWGECSDNI-NH$_2$ | 13 |
| Peptide 5 | Ac-DLVYFELSPDFCA-NH$_2$ | 14 |
| Peptide 6 | Ac-GSKGTQGRACN-NH$_2$ | 15 |
| Peptide 7 | Ac-CNKSGMDGCEL-NH$_2$ | 16 |

These experiments show that the antagonist UM206 is a very potent inhibitor of the canonical Wnt signaling. It is slightly more selective for frizzled-2 over frizzled-1. UM206 is also very specific; it appeared to have no effect on the closely related receptors frizzled-4 and 5 (see FIG. 3, Panel E). UM206(S-S) was found to be a specific agonist for frizzled-1 and frizzled-2, and not for frizzled-4 or frizzled-5 (see FIG. 3, Panel F).

When the peptides according to the invention were tested in a migration assay as disclosed in Example 2 (FIG. 4, Panel A), the antagonist UM206 appeared to counteract the activity of the natural ligands Wnt3a and Wnt5a. Where the natural ligand inhibits migration, the antagonist can block this effect completely (see FIG. 4, Panels B and C, and FIG. 10). This indicates that administration of the antagonist ameliorates migration and, therefore, has a beneficial effect on wound healing. Other applications could be, e.g., skin ulcerations and decubitus, where the normal wound healing process is disturbed.

The peptides were also tested in a differentiation assay as described in Example 3. As is shown in FIG. 5, Panel A, the Wnt/Frizzled signal transduction cascade may influence the differentiation of the fibroblast into the myofibroblast and the other way around. The Wnt/frizzled signal transduction cascade may, as shown in FIG. 5, Panel A, either enhance the amount of α-SMA and, therefore, favor the myofibroblasts or decrease the amount of α-SMA and, therefore, the cells will have a more fibroblast phenotype.

By addition of UM206, not only the increased, but also the decreased, levels of α-SMA can be counteracted, giving all the cells an intermediated cell type resembling the protomyofibroblast. The antagonist, therefore, completely blocks this differentiation (FIG. 5, Panel B).

The antagonist UM206 has a half-life of around 90 minutes in mice and rats, making it a good tool for visualization. Also for therapy, this long half-life makes UM206 an excellent therapeutic composition. A steady state will be reached after +/−10 hours. (See FIGS. 7 and 16.)

In an in vivo model of myocardial infarction (Blankesteijn et al., 1997), a significantly enhanced amount of myofibroblasts (20% in comparison to 4%) was observed. This demonstrates that UM206 has a beneficial effect on infarct healing in vivo.

It will be evident for the skilled person that analogues of UM206 will be equally suited as antagonist of frizzled-1 or frizzled-2 receptors. Such analogues may easily be found by random mutagenesis of the peptide as exemplified herein and testing the mutated peptides in the activity assays as described herein. Analogues may be peptides but peptide mimetics may also be suitable. As an example of how to find analogues, we performed a so-called alanine scan of UM206.

It was found that there are three amino acid residues that are essential; i.e., they cannot be replaced by an alanine residue without affecting the biological activity (see FIG. 8). These residues are threonine, glycine and aspartic acid, which occur at positions 4, 7 and 9 of UM206.

Presence of at least one of the two cysteine residues also appeared to be essential. The cysteine residues were also replaced by alanine residues, by serine residues and by cysteine-alkyl residues. All three replacements revealed the same results in that biological activity was retained when at least one of both cysteine residues were left unreplaced. Replacement of both cysteine residues, however, completely abolished the biological activity. It is concluded that the peptide needs at least one cysteine residue for antagonistic activity.

This shows that the presence of cysteine, threonine, aspartic acid and glycine are essential for the activity of the antagonist. They may, however, be replaced by analogous functional groups, for instance, with respect to size, charge or redox potential, hydrophobicity. This is usually referred to as a conservative substitution.

Hence, the invention relates to a method for antagonizing frizzled-1 or frizzled-2 receptors, wherein the receptor is contacted with a composition comprising a linear fragment of Wnt3, Wnt3a or Wnt5a or a functional analogue thereof, which comprises at least one cysteine residue, one threonine residue, one aspartic acid residue and one glycine residue.

The term "analogue" as used herein is meant to indicate a molecule, preferably a peptide, wherein the essential amino acids are conservatively substituted. Preferably, any substitution mutation is conservative in that it minimally disrupts the biochemical properties of the peptide or analogue thereof. Thus, where mutations are introduced to substitute amino acid residues, positively charged residues (H, K, and R) are preferably substituted with positively charged residues; negatively charged residues (D and E) are preferably substituted with negatively charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys, or Pro. By "hydrophilic" amino acid is meant either Gly, Asn, Gln, Ser, Thr, Asp, Glu, Lys, Arg, or His. This grouping of amino acids can be further subclassed as follows. By "uncharged hydrophilic" amino acid is meant either Ser, Thr, Asn, or Gln. By "acidic" amino acid is meant either Glu or Asp. By "basic" amino acid is meant either Lys, Arg, or His. (See FIG. 6.)

In analogy, the amino acid Cysteine may be replaced by any amino acid that contains a thiol residue such as homocysteine. The amino acid Threonine may be replaced by an amino acid containing a free OH group such as Serine. The amino acid Asparagine may be replaced by an amino acid with an acid group in a side chain and the amino acid Glycine may be replaced by an amino acid with a small neutral side chain, such as Alanine Since several amino acids were found to be dispensable, a particularly useful antagonist according to the invention may also be described as a molecule according to Formula 1:

X-p-Thr-q-Gly-r-Asp-s-Y-T (SEQ ID NO:21)    Formula 1:

wherein X and/or Y is a cysteine residue and p, q, r and s are spacers with a size comparable to zero to ten amino acids and wherein T is a tail consisting of zero to ten amino acids.

The amino acid residues cysteine, threonine, glycine and aspartic acid may be connected through peptide bonds in a peptide structure or by other bonds that provide an appropriate spatial distribution of the important amino acid residues. A spacer with a size comparable to zero to ten amino acid residues is most appropriate.

The tail T is preferably one or more amino acids, which markedly improved the biological activity. The invention, therefore, also relates to a method as described above, wherein a peptide according to Formula 1 is used to antagonize frizzled-1 or frizzled-2 receptors.

The therapeutically relevant steady state concentration of UM206 is about $10^{-9}$ M. UM206 is preferably administered systemically. Oral administration, however, may lead to premature degradation. This hurdle may be circumvented by coatings or modifying the "tail" of the UM206 to increase biostability. Further, in vivo testing may determine an optimal concentration and dose for optimal therapy.

In another embodiment of the invention, UM206 is ready to be used as a screening and visualization tool after coupling with a marker.

The utility of the present invention was further investigated in mice. For that purpose, we developed a frizzled-2 knock-out mouse that mimics the situation of a blocked frizzled receptor. These mice underwent a myocardial infarction and exhibited an ameliorated heart function and a significant increase in myofibroblasts. These myofibroblasts prevented dilatation of the heart and improved the pump function of the heart.

We also synthesized another peptide with amino acid sequence
Peptide UM207:

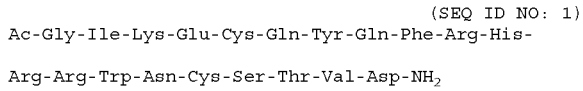

(SEQ ID NO: 1)
Ac-Gly-Ile-Lys-Glu-Cys-Gln-Tyr-Gln-Phe-Arg-His-

Arg-Arg-Trp-Asn-Cys-Ser-Thr-Val-Asp-NH$_2$

This peptide showed comparable characteristics as UM206. When in the linear conformation, UM207 was a potent antagonist, whereas when forced to form a cyclic structure by inducing a S-S bond between the two cysteine residues, UM207 S-S was a potent agonist of the frizzled receptor.

Given the fact that there are also a number of amino acids that can easily be replaced with an Alanine residue, another particularly useful antagonist according to the invention may also be described as a molecule according to the following Formula 2:

Gly-p-X-q-Yr-Thr-s-Asp-T (SEQ ID NO:22)    Formula 2:

wherein X and/or Y is a cysteine residue and p, r and s are spacers with a size comparable to zero to ten amino acids and wherein q is a spacer with a size comparable to five to twenty amino acids and wherein T is a tail consisting of zero to ten amino acids.

Another particularly useful antagonist according to the invention may also be described as a molecule according to the following Formula 3:

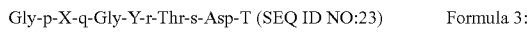

Gly-p-X-q-Gly-Y-r-Thr-s-Asp-T (SEQ ID NO:23)    Formula 3:

wherein X and/or Y is a cysteine residue and p, q, r and s are spacers with a size comparable to zero to ten amino acids and wherein T is a tail consisting of zero to ten amino acids.

The agonistic activity of the cyclic peptides as disclosed herein may also be put to use. Fibrosis of the infarct area is generally considered to be favorable after myocardial infarction, because it can prevent the dilatation of the heart. On the other hand, fibrosis is an unfavorable complication of cardiac remodeling due to, e.g., pressure overload, because stiffening of the ventricular wall leads to filling problems in diastole. These observations illustrate that cardiac fibrosis cannot simply be considered to be good or bad, but that therapeutic modulation of the fibrotic response should depend on the pathological context.

One application of agonists making use of their markedly improved anti-fibrotic effect is, for instance, in cardiac hypertrophy induced by pressure overload. Applications of this agonist could also be found in diseases characterized by excessive fibrosis, e.g., liver fibrosis, lung fibrosis and hypertrophic scarring of the skin after burning injuries.

Another application of the invention is the in vivo determination of the chances of a myocardial infarction. In such a method, a subject is provided with an agonistic or antagonistic compound according to the invention, provided with a label, the compound is allowed to bind to its receptor and the complex between compound and receptor is then visualized in vivo, such as, for instance, by using an MRI scanner. Hence, the invention relates to an in vivo method for the visualization of a frizzled receptor, wherein a composition comprising a frizzled receptor is contacted with a composition comprising a linear or cyclic fragment of Wnt3, Wnt3a or Wnt5a or a functional analogue thereof, which comprises at least one cysteine residue, one threonine residue, one aspartic acid residue and one glycine residue. The more frizzled receptors are detected, the smaller the chances of a myocardial infarction.

Such methods are best performed when the fragment is provided with a detectable label, such as a fluorescent label or an MRI-detectable label.

Panel D: The agonistic activity of UM206(S-S) for frizzled-2. Panel E: Receptor specificity of UM206 Panel F: Receptor specificity of UM206(S-S).

FIG. 4: Panel A: Photographic image of the migration of C-FIT cells (cardiac fibroblasts immortalized with telomerase) in a wound healing assay. Attenuation of migration induced by Wnt can be blocked by adding UM206 in a concentration of $1.10^{-8}$ M as shown in Panels B and C for frizzled-1 and frizzled-2, respectively.

FIG. 5, Panel A: Differentiation of the C-FIT cell line by Wnt3a/Wnt5a.

FIG. 5, Panel B: UM206 blocks the effects of Wnt3a/5a on the differentiation of C-FIT cell line.

FIG. 6: Classification of the amino acids according to physiochemical properties.

FIG. 7: Results of the pharmacokinetics of UM206 in mice.

Figure 8:
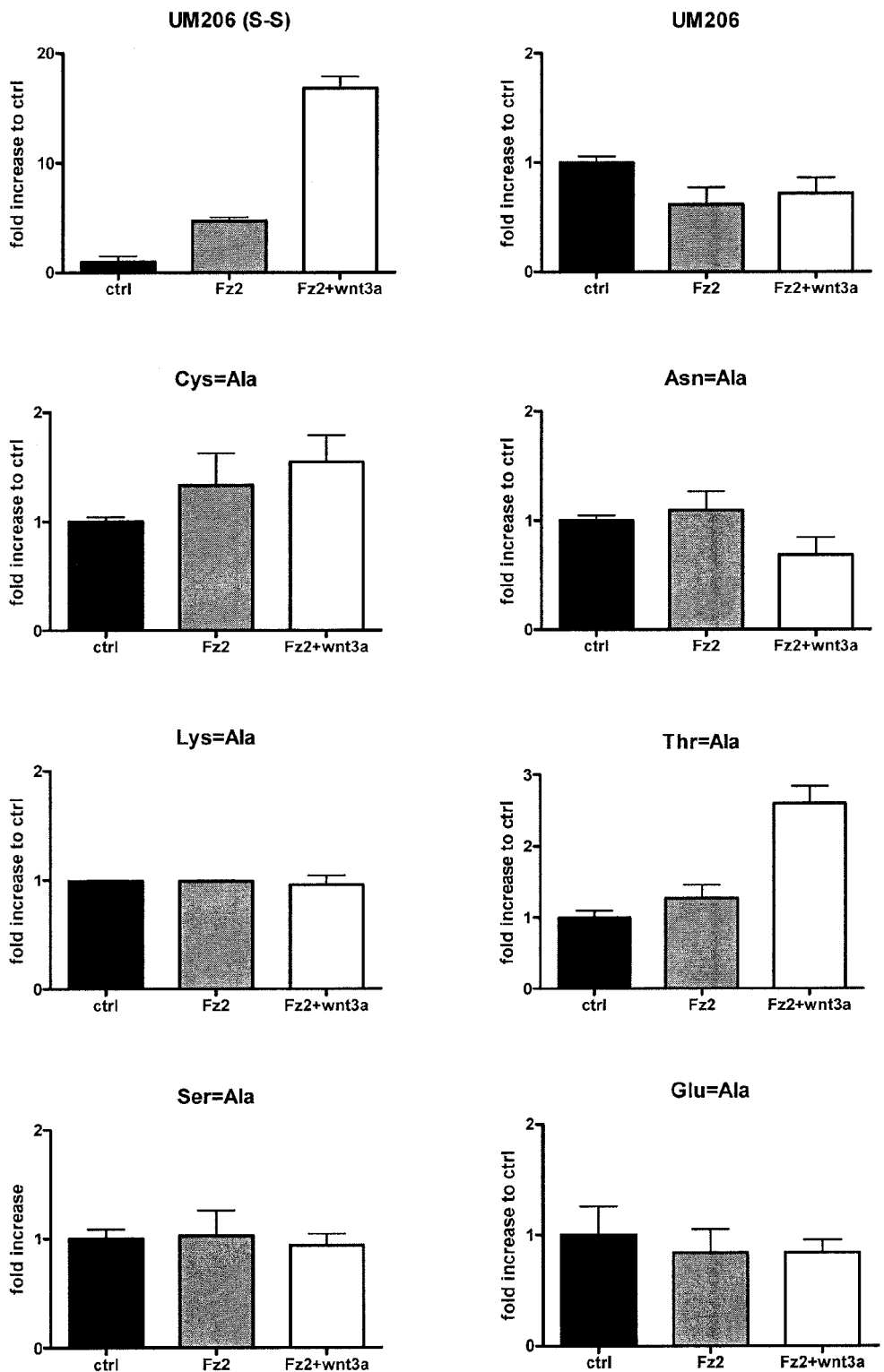
Figure 8:
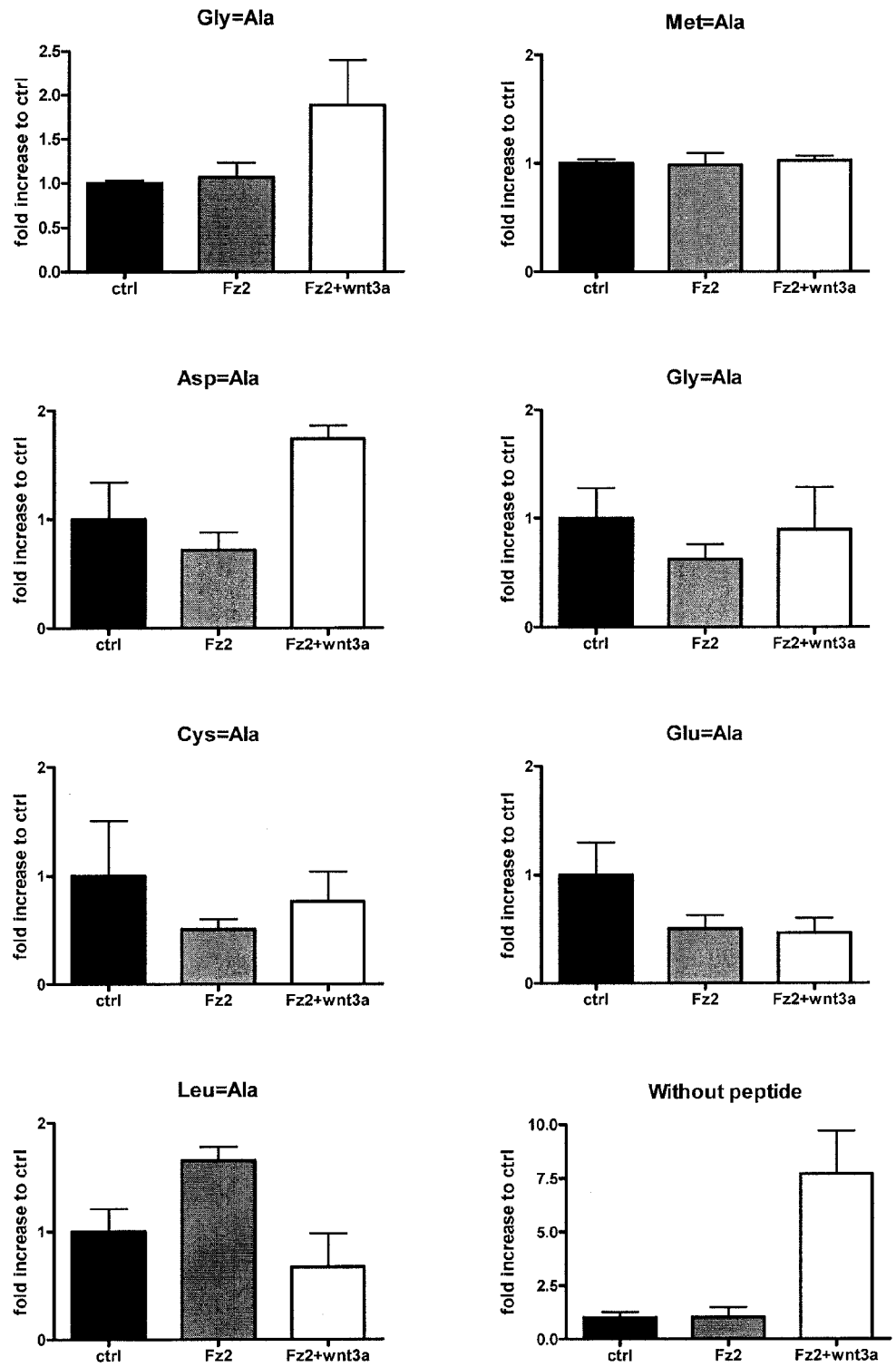

FIG. 8: Alanine scan of UM206.

FIG. 9A: The alignments of Wnt3a (SEQ ID NO: 19) and Wnt5a (SEQ ID NO: 20), two members of the Wnt family that both can bind to frizzled-1 and frizzled-2. Indicated by underline are sequences comprising UM206 (SEQ ID NO: 7), UM207 (SEQ ID NO: 1), and UM208 (SEQ ID NO: 4).

FIGS. 9B through 9D: The inhibitory effects of, respectively, UM206, UM207 and UM208 tested in a HEK superTOPflash cell line. The cells were transfected with either Fzd-1 or -2 as indicated; peptide concentration was $1.10^{-8}$ M. All results are the average of three independent measurements and are represented as means +/−SEM. (***$P<0.001$.)

FIGS. 10A and 10B: Wound assay in which the migration of cardiac fibroblasts immortalized with telomerase (CFIT) into a scratch in the cell layer was studied under different conditions. Overexpression of Fzd-1 or -2 alone or in combination with Wnt3a or Wnt5a significantly attenuated the CFIT migration. This attenuation of the migration could be counteracted by addition of UM206 ($1.10^{-8}$ M). All results are the average of three independent measurements and are represented as means +/−SEM. ($p<0.01$ and *$P<0.001$.)

FIG. 11: Panel A: The Kaplan Meier of the effect of UM206 treatment on the survival rate of mice in which myocardial infarction was induced at t=0. UM206 treatment completely prevented the mortality after infarction, whereas in saline-treated mice, the mortality was ~35% after five weeks. Panel B: UM206 reduced heart failure in the mice that survived for five weeks after MI, as shown by the increased lung weights in the saline-treated group. Panels C.1 and C.2: Echocardiographical measurements like, for example, ejection fraction and end diastolic volume, are indicative of an improved cardiac function in the UM206 treated group. Panels D.1 and D.2: Hemodynamic measurements indicate that cardiac function was significantly better preserved after UM206 treatment. All results are the mean of 26 animals and are represented as means +/−SEM. (*$p<0.05$, $p<0.01$ and *$P<0.001$.)

Figure 12:
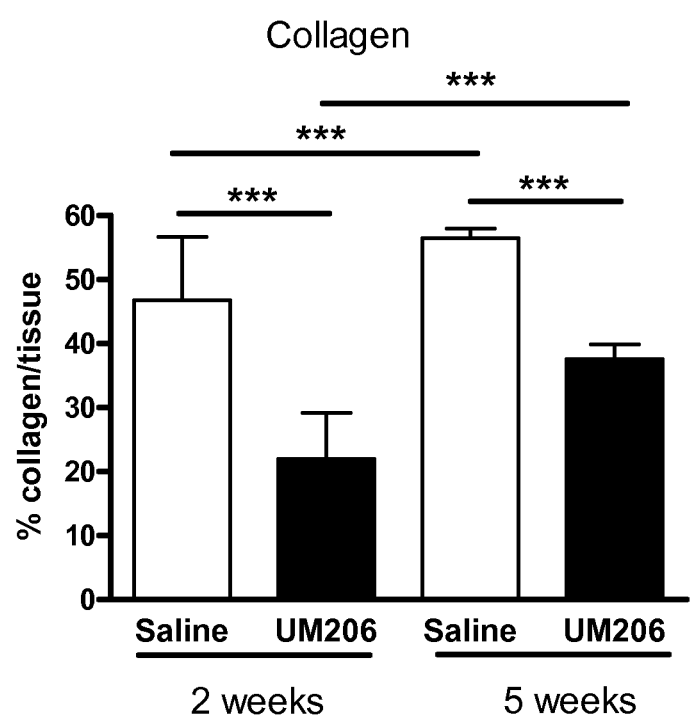

FIG. 12: Panels A.1 and A.2: Transverse sections of a UM206-treated and saline-treated heart, stained with hematoxyline-eosine. The infarcts were less expanded and thicker after UM206 treatment. Panel B: Infarct expansion was decreased, both after two and five weeks. Panel C: Wall thickness of the infarct area, however, was increased in UM206-treated mice. Panel D: The infarct area of UM206-treated mice contained four-fold more myofibroblasts, cells that can actively counteract the dilatation of the infarct area. Panels E.1 and E.2: To support the histological data, ASMA levels were determined both on RNA (qPCR) and protein (Western blot) level. These results confirm the immunohistochemical data, where myofibroblast numbers were found to be increased after UM206 treatment. Panel F: UM206 treatment increases the neovascularization of the infarct area, as reflected by an increased blood vessel/tissue area ratio. Panel G: Collagen content was decreased after UM206 treatment, leading to a less stiff infarct area. All results are the mean of 26 animals and are represented as means +/−SEM. (*$p<0.05$, $p<0.01$ and *$P<0.001$.)

FIG. 13: Blocking of UM206-Rhodamine binding to frizzled-1 and -2 by UM207 and Wnt3a. Panel A: Fluorescent signal of UM206-Rhodamine binding to small intestine and kidney is shown in red, green represents autofluorescence of the tissue. Panel B: Small intestine and kidney imaging after pre-incubation with a high concentration of UM207. Panel C: Small intestine and kidney after pre-incubation with the natural ligand Wnt3a. These images confirm the specificity of UM206 binding.

FIG. 14, Panels A and B: TOPflash experiments to determine the effects of UM206 on the canonical Wnt/Fzd pathway, were repeated in two other cell lines. The data confirmed the HEK superTOPflash data, namely, that UM206 can selectively block canonical Wnt/Fzd-1/2 signaling activated. All results are the average of three independent measurements and are represented as means +/−SEM. (***$P<0.001$.)

FIG. 15: Panels A through C: Inhibition curves for UM206, UM207 and UM208 on HEK209-TOPflash overexpressing cells, transfected with the rFzd-2 receptor and activated with Wnt3a. Curve A was significantly better fitted with by a two-site model, leading to the reported $IC_{50}$ values for the transfected Fzd-2 receptor. Panels D through F: Same experiments with rFzd-1 overexpression. For these experiments, UM208 was dissolved in medium with guanidine to improve solubility. All results are the average of three independent measurements and are represented as means +/−SEM. (***$P<0.001$.)

Figure 16:
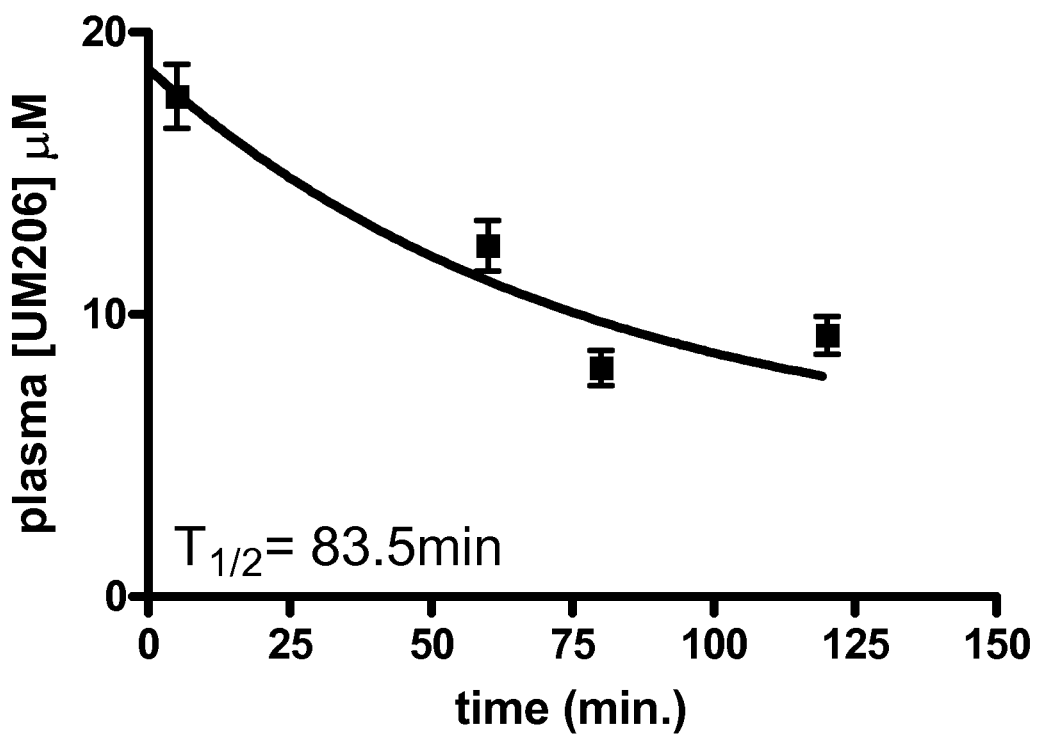

FIG. 16: Pharmacokinetic study, in which UM206 (15 ng) was injected into the tail vein of mice. Blood was sampled at the indicated time points and the amount of UM206 was determined using HPLC, revealing a half-life of 83.5 minutes.

DETAILED DESCRIPTION OF THE INVENTION

Examples

Example 1

Activity Assay

Figure 1:
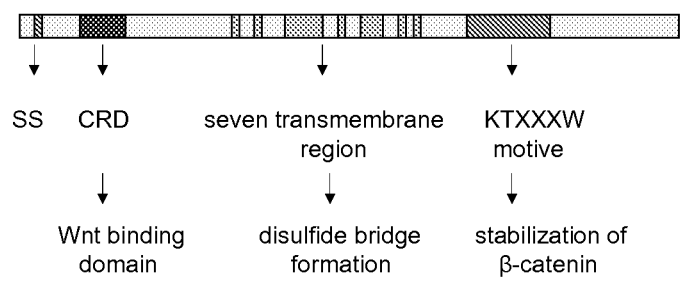
FIG. 1: Schematic representation of the molecular structure of the frizzled receptor and the function of the different domains.
Figure 2A:
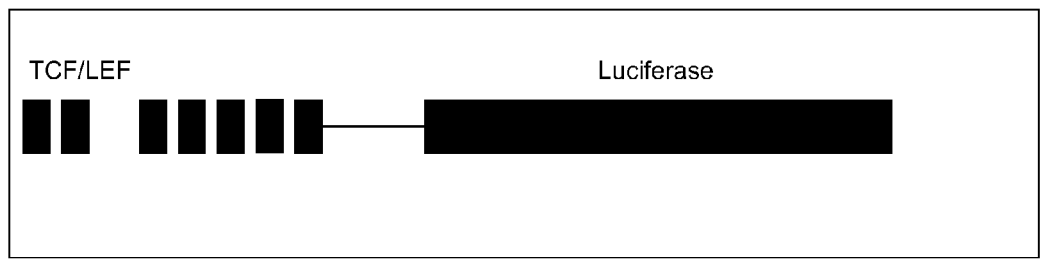
FIG. 2A: Schematic representation of the Topflash: luciferase reporter construct driven by eight TCF/LEF sites (cloned in a MluI site of pTALuc vector).
Figure 2B:
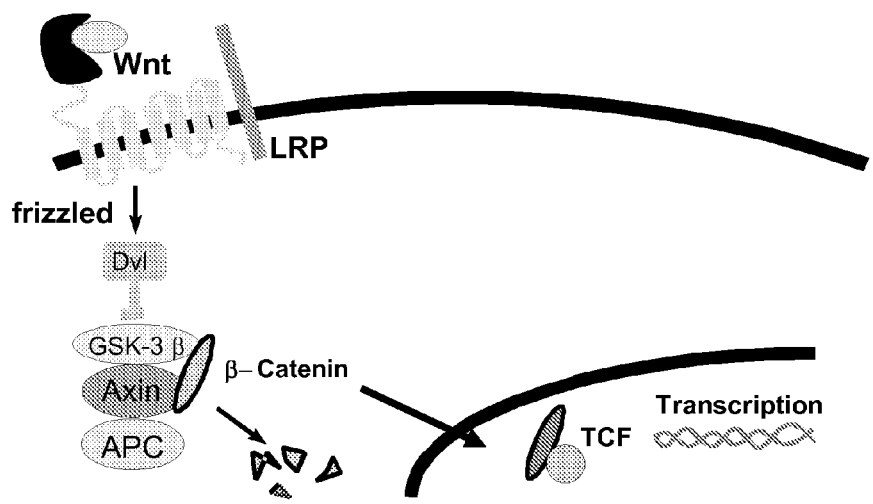
FIG. 2B: Canonical Wnt signaling pathway.

Human embryonic kidney (HEK) cells were used for screening. These cells have a luciferase construct stably transfected into the genome (see FIG. 2A), such that when the frizzled receptor is activated and β-catenin is increased, the luciferase is activated by transcription and light can be measured.

Figure 3:
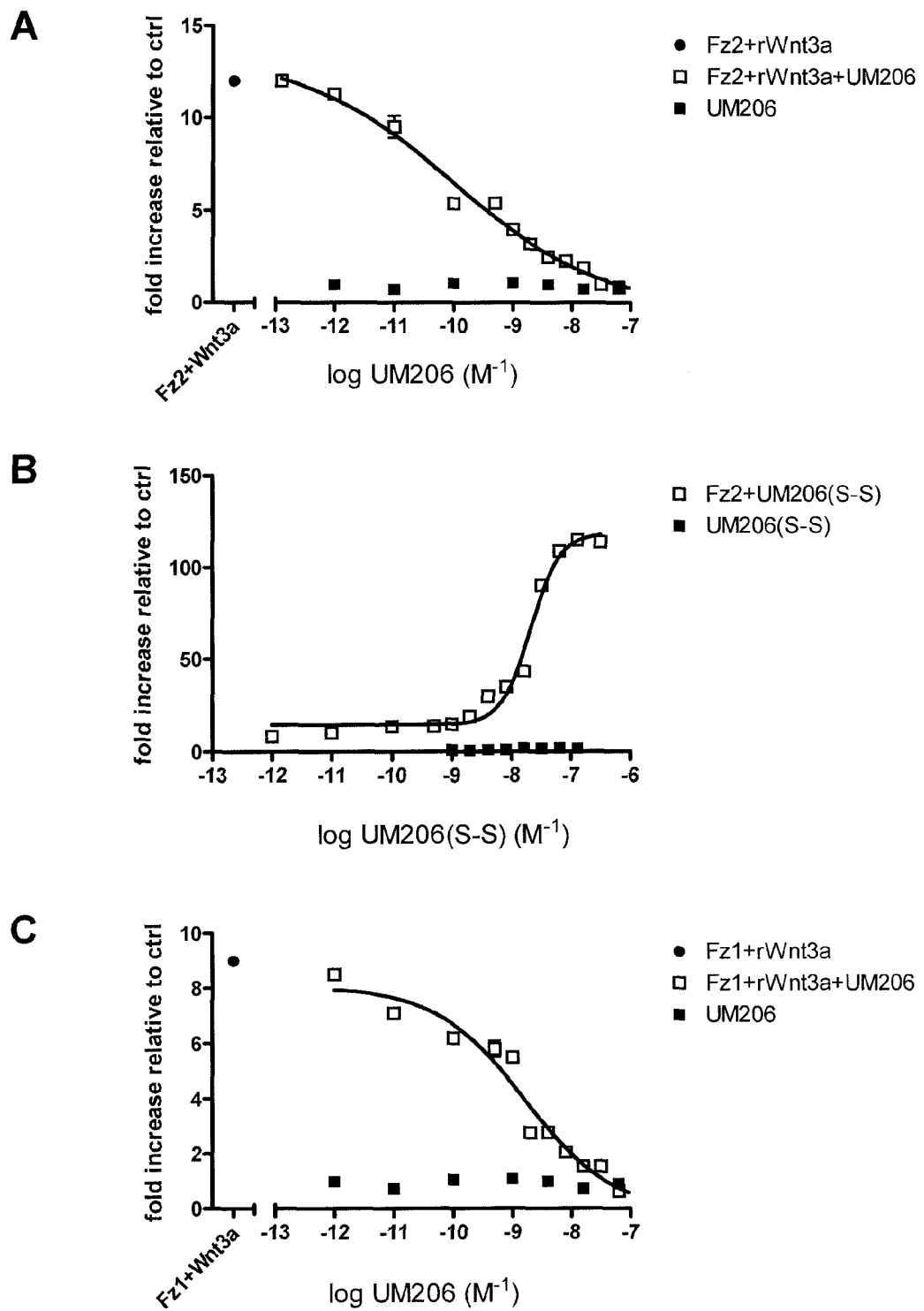
FIG. 3: Panel A: The antagonistic activity of UM206 for frizzled-1. On the y-axis, the fold increase in luciferase activity measured as light units, in comparison to control is depicted; the x-axis shows the concentration of UM206. Panel B: The agonistic activity of UM206(S-S) for frizzled-1 Panel C: The antagonistic activity of UM206 for frizzled-2.

The peptides were tested by transfecting the frizzled-1 or the frizzled-2 receptor and addition of UM206(S-S) to the cell culture. For testing antagonistic activity, UM206 was added and the natural ligand Wnt3a was added, which is a natural stimulus for the canonical pathway. FIG. 3 shows the results for the antagonist UM206.

Example 2

Migration Assay

For this assay, we used rat cardiac fibroblasts, which were immortalized with telomerase, the C-FIT cell line. This cell line was characterized previously and resembles features of primary cardiac fibroblasts. C-FIT cells were plated, treated when they were 70% confluent and a wound was made with a pipette tip at the moment of 100% confluence. Previous research revealed that overexpression of Fz2 with addition of Wnt3a/Wnt5a delayed the much needed migration of the C-FIT cells into the wound.

This assay was first tested with the natural ligand Wnt3a, in combination with frizzled-1 and -2 overexpression. These results clearly indicated that Wnt3a in combination with frizzled-1 or -2 inhibited the migration. Next step was to see whether the antagonist could counteract this. (See FIG. 4.)

UM206 inhibited the delaying effect of the natural ligands and the migration was reset to the migration speed of the control.

Example 3

Differentiation Assay

For this assay, we used the same C-FIT cells as for the migration assay to study a second component of wound healing, namely, differentiation of fibroblasts into myofibroblasts. When wound healing starts, cells called fibroblasts migrate into the scar. These cells have no contractile properties; however, they can differentiate into myofibroblasts, which can actively contract. To study which signals influence the transition from fibroblast into myofibroblasts, we treated the C-FIT cells and harvested them for mRNA isolation. Next, we tested them for the presence of specific markers for myofibroblasts by reverse transcription of the mRNA and subsequent quantitative PCR analysis, which are absent in fibroblasts. One of those markers is α-smooth muscle actin, which makes the cells contract. The results are shown in FIG. 6.

Example 4

Pharmacokinetics Assay

UM206 was injected into the femoral artery of Swiss mice (concentration of $10^{-9}$ M). Blood was sampled at different time points in the femoral vein. The results are shown in FIG. 7. On the y-axis, the concentration of UM206 in the plasma is shown. This is determined with HPLC and the area under the peak is calculated and shown on the y-axis. All values were corrected for the baseline value. (See FIG. 7.)

Example 5

Alanine Scan

Analogues of UM206 were prepared by solid phase peptide synthesis. Each amino acid residue was sequentially replaced by an alanine residue and antagonistic activity of the analogue was tested as described in the activity assay of Example 1. FIG. 8 shows the results for the alanine screening. Titles indicate which amino acid residue was substituted by an alanine residue.

Essential amino acids for antagonistic activity of UM206 were determined by an alanine scan; furthermore, some additional modifications were tested. All peptides were tested at a concentration of 1.10-9 M. These results highlighted four important amino acids, namely: cysteine, threonine, aspartic acid and glycine. Replacement of both cysteines by alanines or serines, or alkylation of both cysteines, abolished the antagonistic properties of UM206. Simultaneous replacement of threonine, aspartic acid and glycine by alanine strongly reduced the antagonistic properties of UM206. The peptide CNVSSHGIDGCDL (SEQ ID NO:18), derived from the area of Wnt3a homologous to UM206, showed antagonistic properties too, albeit that the potency was lower than that of UM206. All results are the average of three independent measurements and are represented as means +/−SEM. (***$P<0.001$.)

Example 6

Cyclization of Linear Peptides

Linear peptides according to the invention may be forced into a cyclic structure at 10 to 100 μM under slightly alkaline conditions at pH 7.5 to 8.5 by aeration under slow bubbling, or stirring, at 5° C. to 25° C. for two hours to four days. Oxidizing agents such as potassium ferricyanide or dimethyl sulfoxide (DMSO) may also be added.

An alternative way to create cyclic peptides is by creating a S—CHR—S— bond, wherein R may be any group but preferably a hydrogen atom. Such a bond may be created by reacting two SH groups with a formaldehyde equivalent, or with an aldehyde RCH=O.

Example 7

Protocols a. Protocols mRNA experiments:
RNA isolation:
solve cells in 1 ml trizol
 ↓5 minutes RT (RT=room temperature)
add 0.4 ml chloroform
 ↓3 minutes RT
 ↓13000 rpm 15 minutes 4° C.
water phase in tube
add 0.5 ml isopropanol
 ↓13000 rpm 10 minutes 4° C.
wash with 0.5 ml 70% EtOH
 ↓13000 rpm 5 minutes 4° C.
Airdry
Solve in 0.05 ml DEPC
 ↓5 minutes 65° C.
Measurement with Nanodrop
cDNA synthesis with iscript:

| iscript | 1 μl |
| iscriptase buffer | 4 μl |
| milliQ | 10 μl |
| mRNA | 5 μl |

PCR protocol:
5 minutes at 25° C.
30 minutes at 42° C.
5 minutes at 85° C.
Hold at 4° C. (optional)
qPCR: SYBR Green Protocol (60° C.):
Master mix/well

| Reagent | stock concentration | volume single reaction |
| --- | --- | --- |
| Master mix | 2X | 12.5 μl |
| Forward primer | 15 pmol/μl | 0.5 μl |
| Reverse primer | 15 pmol/μl | 0.5 μl |

-continued

| Reagent | stock concentration | volume single reaction |
|---|---|---|
| MQ | | 6.5 µl |
| Template | | 5 µl | b. Cells:
  Cell culturing:
  remove medium
  wash with 5 ml PBS
  remove PBS
  add 1 ml trypsine-EDTA
  add 9 ml medium
  put the 10 ml in 15 ml tube
  centrifuge for 5 minutes
  remove medium
  Homogeniseren in 4 ml medium
  1 ml in filterdop 25 cm² flask
  add 20 ml medium
  Herein, the term "medium" describes medium with 10% FCS and 1% gentamycine.
  Transfection and luciferase measurement:
  Day 1:
  Plate cells in 12-well plates
  Day 2: Transfection 12-well plates
  heat Fugene6 and DNA 15 minutes at RT
  2 ml serum-free medium in tube
  add 3µl fugene
  add 2 µg DNA
  incubate 30 minutes at RT
  wash with PBS
  add 50 µtransfectiemix
  add 1 ml antibiotica-free medium
  Day 3: Add conditioned medium or UM206
  Day 4: Luciferase activity measurements
  remove medium
  wash with PBS
  add 500 µl ⅕ lysisbuffer
  shake for 60 minutes
  centrifuge in tube
  20 µl lysaat and 50 µl luciferase in new tube for measurement
  vortex
  measure
  Making of conditioned medium:
  1. spilt the cells 1:10 in 10 ml culture medium without antibiotics and let the cells grow for four days (approximately to confluency)
  2. take off the medium and sterile filter (this is the first batch)
  3. add 10 ml medium without antibiotics and let the cells grow for three days
  4. take off the medium and sterile filter (this is the second batch) stable at 4° C. and can be frozen.
c. Peptide synthesis
  Weigh the peptide
  Weigh the resin
  Make HBTU ratio: 7.6 g in 40 ml
  Wash column with DMF
  Activated 1$^{st}$ peptide by addition of 2 ml HBTU and 0.5 ml TTC (di-isopropyl ethylamine)
  1 minute activating
  10 to 20 minutes peptide on column and stirring
  wash with DMF for 40 seconds (flow wash)
  Two shots of TAA (trifluoroacetic acid) shortly after each other and discard immediately
  2×1 minute TAA on kolom
  Acetylation
  wash with DMSF
  wash with TAA
  Make: A=5 ml DMSF with 0.5 M (236 microliter) acetic anhydride B=5 ml DMSF with 0.5 M (196 microliter) pyridine
  2.5 ml A and 2.5 ml B 2 minutes on kolom
  discard
  2.5 ml A and 2.5 ml B 2 minutes on kolom
  discard
  flow wash DMSF
  formyl group
  wash with 250 ml 20% piperdine in DMSF (8 minutes)
  wash with DMF
  wash with DCM
  wash with DCM/EtOH
d. Migration
  Day 1:
  Plate cells in 12-well plates
  Day 2:
  Transfection (see protocol)
  Day 3:
  Addition of conditioned medium
  Day 4:
  Make a scratch. This is time point zero.
  Making pictures every six hours and analyzing the scratch width.

Example 8

Identification and Pharmacological Characterization of the Peptidergic Fzd Antagonists The alignment of Wnt3a and 5a is shown in FIG. 9A. Three areas of high homology that contained two cysteines are underlined (UM207), (UM208) and (UM206). In FIGS. 9B through 9D, the inhibitory effect of these three peptides on Wnt3a-induced luciferase activity in HEK293-superTOPflash is shown. In each figure, the left set of columns shows that none of the three peptides by itself could induce an increase in luciferase activity in cells, whereas, addition of Wnt3a increases luciferase activity ~450-fold. Transfection of rFzd-1 (middle set of columns) or rFzd-2 (right set of columns) further increased the Wnt3a-induced luciferase activity, an effect that could be blocked almost completely by administration of either UM206 (FIG. 9B), UM207 (FIG. 9C) or UM208 (FIG. 9D) at a concentration of $1 \cdot 10^{-8}$ M. A complete inhibition of Wnt3a-induced TOPflash activation was also observed in CHO and COS-7 cells overexpressing either rFzd-1 or -2, albeit that the fold induction of luciferase activity was considerably lower in these cells. Again, the peptides by themselves had no effect on the luciferase activity. Peptides derived from other regions showed no activity at concentrations up to 10 µM (see Table 3)).

To determine the inhibitory constant of UM206-8, HEK293-superTOPflash cells were transfected with either rFzd-1 or -2 and incubated with Wnt3a ($10^{-9}$M) in the presence of increasing concentrations of either of the peptides (FIG. 15). For UM206, a biphasic inhibition curve was observed that was best fitted with a two-binding-state model. In HEK293-superTOPflash cells transfected with rFzd-2, the high affinity site with an $IC_{50}$ of $1.69 \pm 0.04 \cdot 10^{-11}$ M was most prominent, whereas in rFzd-1 transfected cells, the binding site with an IC50 of $2.1 \pm 0.18 \cdot 10^{-9}$ M was the major binding site. This suggests that UM206 binds to rFzd-2 with an approximate 100-fold higher affinity than to rFzd-1. In contrast, the inhibition curves for UM207 and UM208 were best fitted with a single binding site model; the $IC_{50}$ values for Fzd-2 were $1.52\pm0.08\ 10^{-8}$ M and $2.11\pm0.11\ 10^{-6}$, and for Fzd-1, $4.00\pm0.07\ 10^{-8}$ M and $2.06\pm0.09\ 10^{-6}$ M, respectively. These results clearly show that UM206 has the highest affinity for rFzd-1 and -2, so in the remainder of the experiments, this antagonist was used.

Example 9

UM206 is Selective for Fzd-1 and -2

In FIG. 3, Panel E, the efficacy of UM206 to block the Wnt3a-induced activation of luciferase activity in HEK293 superTOPflash cells transfected with different Fzds is shown. Addition of UM206 in a concentration of $1.10^{-8}$ M abolished the induction of luciferase activity almost completely in cells overexpressing rFzd-1 and -2, but had no effect on cells overexpressing hFzd-4 or -5. This was not due to species differences, because UM206 was fully effective in antagonizing the activation of mouse and human Fzd-1 and -2 by Wnt3a as well (data not shown). From these results, we conclude that UM206 is a high affinity antagonist for Fzd-1 and -2 but that it does not block Fzd-4 and -5 in a relevant concentration range.

Example 10

Structure-Activity Relationship of UM206

In Table 2, the effect of substitution of each of the individual amino acids by alanine on Wnt3a-induced luciferase activity is shown.

TABLE 2

|  | % of inhibition for Fzd-1 | % of inhibition for Fzd-2 |
|---|---|---|
| Wnt3a | 0% | 0% |
| Wnt3a + UM206 | 72.15% | 75.06% |
| Wnt3a + UM206 (1 C = A) | 70.76% | 82.61% |
| Wnt3a + UM206 (2 N = A) | 67.95% | 79.52% |
| Wnt3a + UM206 (3 K = A) | 70.76% | 84.92% |
| Wnt3a + UM206 (4 T = A) | 28.06% | 59.35% |
| Wnt3a + UM206 (5 S = A) | 74.30% | 87.31% |
| Wnt3a + UM206 (6 E = A) | 70.85% | 84.71% |
| Wnt3a + UM206 (7 G = A) | 52.61% | 63.12% |
| Wnt3a + UM206 (8 M = A) | 67.64% | 85.01% |
| Wnt3a + UM206 (9 D = A) | 40.50% | 60.51% |
| Wnt3a + UM206 (10 G = A) | 69.88% | 83.32% |
| Wnt3a + UM206 (11 C = A) | 67.21% | 84.87% |
| Wnt3a + UM206 (12 E = A) | 65.86% | 85.53% |
| Wnt3a + UM206 (13 L = A) | 65.87% | 86.54% |
| Wnt3a + UM206 (C = A) | 0% | 8.39% |
| Wnt3a + UM206 (C = C-alkyl) | 1% | 12.38% |
| Wnt3a + UM206 (C = S) | 0% | 17.00% |
| Wnt3a + UM206 — | 18.00% | 61.16% |
| Wnt3a + UM206 (12-13 EL = AA) | 66.78% | 74.30% |
| Wnt3a + UM206 (4 T = A, 7 G = A, 9 D = A) | 11.25% | 17.52% |
| Wnt3a + CNVSSHGIDGCDL (SEQ ID NO: 18) | 45.32% | 62.41% |

In this experiment, the antagonists were tested in a concentration of $1.10^{-9}$ M, allowing the detection of more subtle changes in antagonistic properties that could remain unnoticed at a concentration of $1.10^{-8}$ M. This Ala-scan showed that replacement of threonine[4], glycine[7] and aspartic acid[9] affected the inhibitory properties of UM206 most strongly. The combination of these three replacements abolished the antagonizing properties almost completely. Substitution of either of the cysteine residues at position 1 or 11 did not affect the antagonistic effect of UM206, but simultaneous substitution of both cysteine residues by either alanine or serine rendered UM206 completely ineffective. Substitution of the C-terminal Glutamic acid and Leucine by an Alanine-Alanine sequence reduced the inhibitory properties of UM206 only slightly, whereas deletion of the C-terminal Glutamic acid and Leucine sequence led to a significant reduction of the potency of UM206. So, we conclude that the antagonistic activity of UM206 is due to the proper spatial positioning of the three amino acid residues Thr, Gly and Asp and to the presence of at least one cysteine residue.

Example 11

UM206 Antagonized Effects of Wnt3a and Wnt5a on Immortalized Cardiac Fibroblasts The overexpression of Fzd-1 and -2 in migrating (myo) fibroblasts during infarct healing was one of the first reports of activation of Wnt/Fzd signaling in cardiovascular remodeling (Blankesteijn 1997). To assess the functional relevance of Wnt/Fzd signaling on cardiac fibroblast proliferation, migration and differentiation, a cardiac fibroblast cell line immortalized with telomerase was used, as previously described (Janhunen 2009, Laeremans 2009). As shown in FIG. 10, administration of either Wnt3a or Wnt5a attenuated the migration of cardiac fibroblasts immortalized with telomerase (CFIT) overexpressing either rFzd-1 or -2 (Panels A and B, respectively). The effects of Wnt proteins on cell migration were blocked completely by addition of UM206 ($1.10^{-8}$ M) to the culture medium.

Example 12

UM206 Reduced Ventricular Remodeling and Prevented Heart Failure Development After Myocardial Infarction in Mice In order to determine the pharmacokinetic properties of UM206, we injected 15 ng of the compound into the tail vein of mice and monitored the concentration in the blood at different time points. The half-life turned out to be $83.5\pm1.63$ minutes (n=24; see FIG. 16). This half-life, combined with the high affinity of UM206 allowed us to test its effects on infarct healing in mice. To this end, we administered UM206 subcutaneously by an osmotic minipump (6 microgram/kg/day); the control group was equipped with a saline-filled minipump. The minipumps were implanted at the time of infarct induction and lasted for up to five weeks. UM206 administration offered a dramatic improvement of survival: at five weeks after MI, 35% of the saline-treated mice had died, whereas not a single mouse had died in the UM206-treated group (FIG. 11, Panel A). Post-mortem analysis revealed that the mortality in the saline-treated group was due to heart failure, as diagnosed by a wet, foamy aspect of the lungs and severely elevated wet lung weight. In the surviving saline-treated mice, wet lung weight was 40% higher than in the UM206-treated mice at five weeks post-MI, suggesting development of heart failure in the surviving saline-treated mice as well (FIG. 11, Panel B). Echocardiography showed a doubling of the ejection fraction and a 40% reduction in end diastolic volume of the left ventricle in the UM206-treated group, all indicative for a better preservation of cardiac function (FIG. 11, Panels C.1 and C.2). Further details of the echocardiographic analysis are provided in Table 4.

TABLE 4

Echocardiographic parameters of mice treated with UM206 compared to saline-treated mice.

|  |  | Saline | | UM206 | |
| --- | --- | --- | --- | --- | --- |
|  |  | AVG | SEM | AVG | SEM |
| LVAd | $cm^2$ | 0.50 | 0.01 | 0.38 | 0.01 |
| LVLd | cm | 0.97 | 0.01 | 0.91 | 0.02 |
| LVAs | $cm^2$ | 0.44 | 0.01 | 0.30 | 0.02 |
| LVLs | cm | 0.93 | 0.10 | 0.86 | 0.01 |
| AoD | cm | 0.19 | 0.01 | 0.18 | 0.01 |
| LVLd | cm | 1.01 | 0.02 | 0.95 | 0.01 |
| LVLs | cm | 0.97 | 0.02 | 0.89 | 0.01 |
| IVSd anterior wall | cm | 0.03 | 0.01 | 0.07 | 0.03 |
| IVSd posterior wall | cm | 0.07 | 0.01 | 0.09 | 0.01 |
| LVIDd | cm | 0.71 | 0.01 | 0.59 | 0.01 |
| IVSs anterior wall | cm | 0.04 | 0.01 | 0.07 | 0.01 |
| IVSs posterior wall | cm | 0.10 | 0.01 | 0.14 | 0.01 |
| LVIDs | cm | 0.65 | 0.01 | 0.52 | 0.01 |
| EDV_L | $cm^3$ | 0.214 | 0.02 | 0.132 | 0.003 |
| ESV_L | $cm^3$ | 0.179 | 0.007 | 0.090 | 0.017 |
| SV_L | $cm^3$ | 0.035 | 0.005 | 0.041 | 0.014 |
| EF_L | % | 16.50 | 0.30 | 31.4 | 0.40 |
| FS | % | 8.60 | 0.50 | 13.20 | 0.85 |
| IVS anterior | % | 10.10 | 0.80 | 8.10 | 0.76 |

Cardiac function was further assessed using a Millar pressure recording catheter inserted into the left ventricle. The tangents on the pressure time curve were significantly steeper in the UM206-treated groups, resulting in a higher positive dP/dt and a lower negative dP/dt value (FIG. 11, Panels D.1 and D.2). Additional hemodynamic parameters are presented in Table 5. These observations further underscore the beneficial effect of UM206 treatment on cardiac function post-MI.

TABLE 5

Hemodynamic measurements.

|  |  | Saline | | UM206 | |
| --- | --- | --- | --- | --- | --- |
|  |  | AVG | SEM | AVG | SEM |
| Heart rate | beats/min | 78.75 | 4.79 | 106.32 | 4.63 |
| Systolic pressure | mmHg | 26.06 | 9.61 | 27.93 | 10.41 |
| Diastolic pressure | mmHg | 1.73 | 0.12 | 1.27 | 0.17 |
| Left ventricular pressure | mmHg | 8.69 | 0.24 | 10.14 | 3.74 |
| Maximum positive slope | mmHg/sec | 3584 | 152.97 | 5343.84 | 216.63 |
| Pressure of positive slope | mmHg | 15.87 | 5.76 | 17.78 | 6.38 |
| Maximum positive slope/pressure | 1/sec | 43.78 | 1.93 | 69.13 | 3.82 |
| Maximum negative slope | mmHg/sec | −2276.25 | 90.03 | −2542.08 | 108.40 |
| Pressure of negative slope | mmHg | −12.07 | 0.53 | −9.44 | 0.57 |
| Maximum negative slope/pressure | 1/sec | 33.29 | 1.14 | 32.84 | 4.88 |

All results are the mean of 26 animals and are presented as means +/− SEM.

Example 13

UM206 Treatment Improved the Characteristics of the Infarct Area

Macroscopic analysis of longitudinal sections of the infarcted hearts revealed that UM206 treatment profoundly reduced infarct expansion and ventricular dilatation (FIG. 12, Panels A.1 and A.2) compared to saline treatment. This was confirmed by histological analysis of the infarct area. The infarct areas were significantly smaller in UM206-treated compared to saline-treated mice (FIG. 12, Panel B), both at 2 and 5 weeks after MI. Moreover, as shown in FIG. 12, Panel C, the infarct areas were significantly thicker in the UM206-treated mice at both time points. Myofibroblast numbers were more than four-fold higher in the UM206-treated mice at two weeks post-MI as compared to saline-treated mice. In both groups, we observed a similar decline in myofibroblast numbers between two and five weeks post-MI, resulting in a significantly elevated number at five weeks post-MI in the UM206-treated group (FIG. 12, Panel D). The higher myofibroblast numbers in the UM206-treated group could be confirmed by significantly higher a-SMA levels in the five-week-old UM206-treated infarcts, as determined by qPCR (FIG. 12, Panel E.1) and Western blotting (FIG. 12, Panel E.2). These results suggest that an increased myofibroblast content contributes to the reduced infarct expansion and subsequent ventricular dilation in the UM206-treated groups. Moreover, UM206 treatment (five weeks) resulted in an increased amount of blood vessels (FIG. 12, Panel F) and reduced collagen levels (FIG. 12, Panel G) in the infarct area, compared to saline treatment. In our experiments, we did not observe any effects of UM206 on other organs known to contain Fzd-2, including kidney and small intestine. QPCR of several Wnt target genes revealed no difference in the expression levels of these genes in animals treated with UM206 for five weeks (see Tables 6 and 7).

TABLE 6

Expression patterns of different genes in the small intestine to study any potential effect of long-term UM206 administration on intestinal tissue.

|  | Saline | | UM206 | | |
| --- | --- | --- | --- | --- | --- |
| Gene | Rel. exp. | SEM | Rel. exp. | SEM | significance |
| Ascl 2 | 1.44 | 0.01 | 1.42 | 0.01 | — |
| Dvl 2 | 1.13 | 0.03 | 1.13 | 0.04 | — |
| Inos | 1.19 | 0.01 | 1.18 | 0.02 | — |
| Col I | 1.35 | 0.01 | 1.32 | 0.01 | — |
| CD 44 | 1.27 | 0.02 | 1.22 | 0.02 | — |
| Axin 2 | 1.08 | 0.04 | 1.05 | 0.04 | — |
| Itm 2A | 0.99 | 0.05 | 0.97 | 0.05 | — |
| Mmp 2 | 1.34 | 0.01 | 1.32 | 0.01 | — |

These data indicate that UM206 had no influence on the expression patterns in the small intestine.

TABLE 7

Similar experiment on kidney.

|  | Saline | | UM206 | | |
| --- | --- | --- | --- | --- | --- |
| Gene | Rel. exp. | SEM | Rel. exp. | SEM | significance |
| Twist | 1.45 | 0.03 | 1.49 | 0.03 | — |
| α-actin | 1.04 | 0.01 | 1.06 | 0.02 | — |
| LEF | 1.66 | 0.02 | 1.70 | 0.09 | — |
| FN | 1.62 | 0.01 | 1.66 | 0.01 | — |
| Col I | 1.38 | 0.03 | 1.39 | 0.01 | — |
| α-SMA | 1.18 | 0.03 | 1.21 | 0.04 | — |

TABLE 7-continued

Similar experiment on kidney.

| Gene | Saline Rel. exp. | SEM | UM206 Rel. exp. | SEM | significance |
|---|---|---|---|---|---|
| DDK 1 | 1.83 | 0.01 | 1.87 | 0.01 | — |
| DDK 2 | 1.40 | 0.01 | 1.44 | 0.01 | — |
| DDK 3 | 0.85 | 0.01 | 0.87 | 0.01 | — |

These data indicate that UM206 had no influence on gene expression in the kidney.

Example 14

Blocking of Rhodamine-Labeled UM206 Binding by UM207 and Wnt3a

To demonstrate that the binding site of UM206 on Fzd-1 and -2 is shared with UM207 and Wnt3a, we developed rhodamine-labeled UM206. Attachment of rhodamine to $Lys^3$ of UM206 did not affect its $IC_{50}$ value for blocking Wnt3a-induced luciferase expression in HEK293 superTOP-flash cells (not shown). As shown in FIG. 13, incubation of frozen sections of mouse kidney and gut with UM206-rhodamine ($1.10^{-8}$ M) for 15 minutes, followed by rinsing in ice-cold PBS, revealed staining of tubular epithelium and panneth cells as assessed by two-foton microscopy. Specificity of the binding site was confirmed by prior incubation of the tissue sections with UM207 ($1.10^{-8}$ M) or recombinant Wnt3a ($1.10^{-8}$ M). Both compounds completely abolished the binding of UM206-rhodamine to its receptors. These data strongly suggest that UM206 and UM207 utilize a binding site on Fzd-1 and -2 that is also occupied by Wnt3a.

Example 15

Discussion

Herein, we describe the design of antagonists for Fzd-1 and -2, based on areas of high homology between Wnt3a and -5a. Based on a set of pre-defined criteria, we identified three peptidergic antagonists, which all could block the activation of Fzd-1 and -2 by Wnt3a and Wnt5a; we named the peptides UM206-8. Because the $IC_{50}$-value of UM206 for Fzd-1 and -2 was lower than that of UM207 and UM208, we focused on UM206 in the remainder of the studies. All three peptides feature two cysteines separated by four to ten amino acids. The Gly, Asp and Thr residues are present in all three peptides and were shown to be important in the blocking effect of UM206. Either of the two cysteines of UM206 could be replaced by alanine with little consequences for the binding, but replacing both cysteines caused complete loss of activity. UM206 blocked Fzd-1- and -2-mediated Wnt signaling effectively in HEK293 superTOPflash, COST and CHO cells, as well as cardiac fibroblasts immortalized with telomerase. Moreover, UM206 administration had a beneficial effect on infarct healing by increasing myofibroblast and blood vessel numbers in the infarct area, preventing dilatation of the left ventricle, improving cardiac function and completely preventing heart failure. Finally, by using rhodamine-labeled UM206, we could show that UM206 and UM207 occupy the same binding site, which is also used by Wnt3a.

Because of the lack of pharmacological tools to intervene in Wnt/Fzd signaling in vivo, only genetic interventions have been reported so far in studies on the role of Wnt signaling in infarct healing. Barandon et al. were the first to show a beneficial effect of overexpression on infarct healing of FrzA, a bovine homologue of soluble frizzled-related protein-1 (sFRP1). They observed a decreased infarct size with elevated numbers of myofibroblasts and increased angiogenesis in the infarcted FrzA transgenic mice (Barandon et al., 2003), which could be confirmed in the present study using an Fzd-1 and -2 antagonist. Interestingly, a reduction in infarct rupture frequency was also observed in the FrzA transgenic mice. In contrast, UM206 treatment of 129S6 mice, a mouse strain with infarct rupture frequency of ~60% (van den Borne et al., 2009), did not reduce the number of ruptured infarcts (H. Laeremans, unpublished observations). This suggests that sFRP may not solely act by blocking of Wnt signaling but by additional mechanisms as well. In the mean time, the beneficial effects of sFRP overexpression on infarct healing have been confirmed by Kobayashi et al. (Kobayashi et al., 2009). Taken together, these reports support the observations of the present study and point to a beneficial effect of inhibiting Wnt/Fzd signaling on the wound-healing process after MI. We did not observe any adverse effects of chronic UM206 administration, indicating that this therapeutic intervention is safe and does not interfere with normal physiological processes.

One of the most likely molecular targets of UM206 appears to reside in the myofibroblasts in the infarct area. The role of myofibroblasts in wound healing and tissue repair is well established. These cells are responsible for the contraction of skin wounds, thereby limiting the size of the scar that is formed at the site of injury (Hinz, 2007; Hinz et al., 2007). More recently, a similar role has been described for myofibroblasts in the infarct area (Ertl and Frantz, 2005; Frangogiannis, 2006; Squires et al., 2005; van den Borne et al., 2010), thereby preventing expansion of the infarct area (Hutchins and Bulkley, 1978). In a study on the effect of genetic background on infarct healing in the mouse, we observed an inverse relationship between myofibroblast content and infarct dilatation (van den Borne et al., 2009). Moreover, myofibroblasts remain present in well-healed human infarcts for decades, but are scarce in dilated infarcts obtained from heart failure patients (Cleutjens et al., 1999; Willems et al., 1994). Previously, we have shown that myofibroblasts express Fzd-1 and -2 during their migration into the infarct area (Blankesteijn et al., 1997). Overexpression of components of the Wnt/Fzd pathway affect the differentiation and migration of cardiac fibroblasts immortalized with telomerase (H. Laeremans et al., manuscript submitted). Therefore, we conclude that the Fzd-1 and -2 expressed on myofibroblasts during infarct healing play a functional role in the wound healing process after MI and can serve as a therapeutic target for intervention in this process. Moreover, the results of the present study highlight the importance of targeting (myo) fibroblasts to preserve cardiac function in the remodeling heart (Brown et al., 2005; Sun et al., 2002). UM206 may well serve as a lead for the development of drugs that address this target. This is of particular importance because the drugs that are currently available to treat infarct healing post-MI have pleiotropic effects on inflammation, extracellular matrix deposition and cardiac remodeling (Jugdutt, 2008).

In this study, we used rhodamine-labeled UM206 to investigate the binding site of UM206 and UM207 on Fzd-1 and -2 in kidney and small intestine. The binding of rhodamine-labeled UM206 could be prevented by preincubation with either Wnt3a or UM207. These experiments provide the pharmacological evidence that UM206 and UM207 use the same binding site on the Fzd protein. Moreover, this binding site is also used by Wnt3a. These data suggest that UM206 and UM207 act as competitive antagonists for Wnt3a.

The biological activity of peptides derived from Wnt5a has been shown previously by Säfholm et al. (Säfholm et al., 2005). In this study, an anti-migratory effect of these peptides on breast cancer cells was observed. Although their peptide, named FOXY5, is identical to the C-terminal 6 amino acids of UM206, its site of action appears to be distinct from that of UM206 for several reasons: 1) The activity of FOXY5 was sensitive to a Fzd-5 blocking antibody, whereas UM206 interacts with Fzd-1 and -2 but not with Fzd-5.2) Substitution of the only cysteine residue in FOXY5 with alanine did not affect its binding, whereas in UM206, at least one cysteine has to be present for biological activity. 3) FOXY5 actively inhibited breast cancer cell migration, thereby acting as a Wnt5a mimetic, whereas UM206 alone had no effect on cell migration and acts as a Wnt3a/5a antagonist. 4) FOXY5 and related peptides are active at concentrations of 10 to 100 whereas the $IC_{50}$ for UM206 is in the nanomolar range.

In conclusion, the results of the present study clearly show that pharmacological targeting of Fzd proteins can be a successful and safe approach to intervene in pathological processes such as myocardial infarction. In the mean time, the role of Wnt/Fzd signaling has been implicated in processes as diverse as stem cell differentiation (Reya and Clevers, 2005; Säfholm et al., 2005), tumor metastasis (Lai et al., 2009), bone metabolism (Piters et al., 2008) and various neurological disorders (De Ferrari and Moon, 2006). This calls for an extensive search for ligands for the different Fzd proteins involved in these diseases.

Example 16

Materials

The HEK superTOPflash cell line was kindly provided by J. Nathans and CHO and COS-7 cells were obtained from DSMZ, Braunschweig, Germany. The CFIT cell line was developed and characterized in our lab (Janhunen et al., 2009). The TOPflash construct is from Upstate (Millipore, Billerica Mass., USA). The peptides were synthesized in our lab, but large-scale synthesis of UM206 was performed by ChemPep, Miami Fla., USA.

Example 17

Cell Culture and Transient Transfection

The cell lines were cultured in 75 cm² culture flasks (Corning, Schiphol, the Netherlands) in Dulbeco's modified essential medium with L-glutamine (2 mM), 10% fetal calf serum (Invitrogen, Merelbeke, Belgium), and 1% gentamycin (Sigma-Aldrich, Zwijndrecht, The Netherlands). Before starting the experiment, the cell lines were treated with plasmocin 25 µg/ml (Invivogen, Toulose, France) and tested with a mycoalert mycoplasma detection kit (Lonza, Rockland Me., USA). Cells were transiently transfected with Fugene6 (Roche, Indianapolis Ind., USA) with plasmid DNA, pcDNA3.1/hygro (Invitrogen) with frizzled-1/2/4 or Wnts 3a-5a or with pcDNA3.0 (Invitrogen) containing the β-catenin or frizzled-5 sequence. After transfection, the cells were cultured for 24 hours in conditioned medium, collected from the cultured L-cells, L-cells with Wnt3a or 5a (Invitrogen). At the same moment the antagonist was added.

Example 18

Peptide Fragment Synthesis

All peptide fragments were synthesized by manual solid-phase peptide synthesis on a 0.3-0.4 mmol scale using the in situ neutralization/activation procedure for Boc-/Bzl-peptide synthesis as previously described (Schnolzer et al., 1992), but using HCTU instead of HBTU as a coupling reagent. MBHA-polystyrene resin (1 meq/g) was used as the solid support.

The peptides were deprotected and cleaved from the resin by treatment with anhydrous HF for one hour at 0° C., using 4 v-% p-cresol as a scavenger.

Following cleavage, the peptides were precipitated with ice-cold diethylether, dissolved in aqueous buffer containing 6 M Gn.HCl, 0.1 M sodium acetate buffer (pH 4) and purified by semi-preparative reversed-phase HPLC. Fractions containing the desired product were identified by ESI-MS, pooled and lyophilized.

Example 19

Luciferase Experiments

For the luciferase experiments not in HEK cells, the cells were additionally transfected with a TOPflash construct, eight TCF/LEF binding sites cloned into the pTA-Luc vector. Luciferase activity was measured using luciferase assay system (Promega, Madison Wis., USA).

Example 20

Migration Assay

Cells were plated on day 0, and cultured until 70% confluence before transfection or treatment. Migration assays started 48 hours after transfection and/or treatment. The time point where the scratch was made, is indicated as 0 hours. Scratch width was measured at this time point, and also after 6, 12, and 24 hours.

Example 21

Quantative PCR

RNA was isolated using the Trizol method (Invitrogen). For the RT-PCR, the RNA was transcribed to cDNA with iscript™ cDNA synthesis kit (Bio-Rad, Hercules Calif., USA), Syber green (Eurogentec, Ghent, Belgium) was used for the detection of cDNA levels and cyclophilin served as the house keeping gene. In Supplementary methods panel 5, the primer sequences are shown.

Example 22

Western Blots

For Western blot, cells were homogenized in ice-cold Laemmli buffer and protein content was measured using the BCA protein assay (Pierce Biotechnology Inc., Rockford Ill., USA); proteins were denatured by boiling, separated on a 10% SDS-page gel, and transferred onto a Hybond C nitrocellulose membrane (Amersham Biosciences, Little Chalfont, United Kingdom). After blocking, membranes were incubated overnight at 4° C. with primary antibodies against β-catenin, α-SMA (both 1:2000, BD Biosciences, Franklin Lakes N.J., USA) or β-actin (1:2000 Sigma-Aldrich). Anti-mouse immunoglobulin G 1/5000 (Vector Labs Inc.) was used as the secondary antibody, and the membranes were developed using the Supersignal West Pico chemiluminescence kit (Pierce). Images of the blots were analyzed with image analysis software (Qwin Leica, Cambridge, United Kingdom).

Example 23

Animal Surgery

Male Swiss mice were used (10-12 weeks of age, Charles River, Maastricht, The Netherlands). The animals were randomly included into the three different experimental groups. For the pharmacokinetics, animals had a venous cannula where a bolus injection of UM206 was given and blood samples were collected. In the treatment study, either UM206 (6 µg/kg/day) or saline were administered by an osmotic minipump (Alzet 2002 or 2006 for two-and five-week treatments, respectively; Alzet, Cupertino Calif., USA). MI was induced, under isofluorane anesthesia as previously described (van den Borne et al., 2009). All experimental procedures were approved by the Committee for Animal Research of Maastricht University.

Example 24

Echocardiography

All animals were subjected to extensive echocardiography studies for the assessment of myocardial infarct size, LV cavity dimensions and ventricular function. Echocardiography examination was performed under 2% isofluorane. Echocardiograms were recorded with Philips Sonos 5500 ultrasound system (Philips, Eindhoven, the Netherlands) using a 20-MHz linear probe.

Example 25

Hemodynamic Measurements

The animals were anaesthetized with urethane (2.5 m/g body weight, i.p., Sigma-Aldrich) followed by intubation and connected to a rodent ventilator (Hugo Sachs, March-Hugstetten, Germany). Body temperature was maintained at 37° C. The mice were then allowed to stabilize prior to hemodynamic measurements. A high-fidelity catheter tip micromanometer (Mikro-tip1.4F, SPR-671; Millar Instruments, Houston TX, USA) was inserted through the right carotid artery into the left ventricular cavity. Ventricular pressure was measured. Maximal positive and negative pressure development (+dP/dt and −dP/dt) and heart rate were determined on a beat-to-beat basis. The heart was then stimulated by an i.v. ramp-infusion of dobutamine (Sigma-Aldrich) using a microinjection pump (Model 200 Series, KdScientific, Boston, Mass., USA).

Example 26

HPLC

Blood samples were collected from the animals for the pharmacokinetics and after 14 to 35 days treatment, to determine the concentration of UM206. Blood was centrifuged and the plasma was treated with 1% TFA.

Analytical HPLC was performed using a Vydac C18 RP-HPLC column (4.6 min×150 mm, 1 mL/minute flow rate) connected to a Varian Prostar system consisting of two Varian Prostar 215 delivery modules and a Varian Prostar 320 UV/Vis detector (214 nm). A linear gradient of 0% to 67% buffer B in buffer A over 30 minutes was used, where buffer A=0.1 v-% TFA in $H_2O$ and buffer B=0.1 v-% TFA, 10 v-% $H_2O$ in $CH_3CN$.

Semi-preparative HPLC was performed using Vydac C18 RP-HPLC columns (10 mm×250 mm, 5 mL/minute flow rate or 22 mm×250 mm, 10 mL/minute flow rate) connected to a Waters Deltaprep System consisting of a Waters Prep LC Controller and a Waters 2487 Dual wavelength Absorbance Detector (214 nm). Peptides were eluted using a shallow gradient of B in A, based on an exploratory analytical HPLC run.

Product-containing fractions were analyzed by Electrospray Ionization Mass Spectrometry (ESI-MS), pooled and lyophilized Mass Spectrometry. ESI-MS was performed on an Applied Biosystems SCIEX API 150 EX electrospray ionization quadrupole (ESI-Q) mass spectrometer. Peptide masses were calculated from the experimental mass to charge (m/z) ratios from all the protonation states observed in the ESI-MS spectrum of a peptide using Analyst 1.4.2 software (Sciex).

Example 27

Immunohistochemical Staining

One-half of the hearts of the mice was embedded in paraffin and cut in 4 µm sections. The paraffin sections were rehydrated and washed in PBS. One section was stained with AZAN, allowing an accurate determination of the infarct size. To visualize the myofibroblasts in the infarct area, the sections were incubated with an antibody directed against a-smooth muscle actin (Sigma-Aldrich), followed by incubation with the peroxidase-conjugated secondary antibody (Vector laboratories). Nuclei were visualized by hematoxylin. Photos were taken with a Leica (CTR500, 63x/0.85) camera and analyzed with the Quantimet program (QWin/QGo). An examiner blinded to the groups of the animals obtained all measurements. For the experiments with Rhodamine-labeled UM206, frozen sections (4 µm) of mouse kidney and small intestine were used.

Example 28

Statistical Analysis

All values are shown as mean±S.E.M. Differences between groups were examined for statistical significance using two-way ANOVA with the Bonferroni post-test or unpaired student T-test (Graph Pad Prism). A P value less than 0.05 was considered as a statistically significant difference.

REFERENCES

Blankesteijn W. M., Y.P. Essers-Janssen, M. M. Ulrich, and J. F. Smits, 1996. Increased expression of a homologue of drosophila tissue polarity gene "frizzled" in left ventricular hypertrophy in the rat, as identified by subtractive hybridization. *J. Mol. Cell Cardiol.* 28:1187-91.

Blankesteijn W. M., Y.P. Essers-Janssen, M. J. Verluyten, M. J. Daemen, and J.F. Smits, 1997. A homologue of Drosophila tissue polarity gene frizzled is expressed in migrating myofibroblasts in the infarcted rat heart. *Nat Med.* 3:541-4.

Brack A. S., M. J. Conboy, S. Roy, M. Lee, C. J. Kuo, C. Keller, and T. A. Rando, 2007. Increased Wnt signaling during aging alters muscle stem cell fate and increases fibrosis. *Science* 317:807-10.

Imai K., M. Morikawa, J. D'Armiento, H. Matsumoto, K. Komiya, and Y. Okada, 2006. Differential expression of Wnts and FRPs in the synovium of rheumatoid arthritis and osteoarthritis. *Biochem. Biophys. Res. Commun.* 345:1615-20.

Konigshoff M., N. Balsara, E. M. Pfaff, M. Kramer, I. Chrobak, W. Seeger, and O. Eickelberg, 2008. Functional Wnt signaling is increased in idiopathic pulmonary fibrosis. *PLoS ONE.* 3:e2142.

Li Y., W. Foster, B. M. Deasy, Y. Chan, V. Prisk, Y. Tang, J. Cummins, and J. Huard, 2004. Transforming growth factor-beta1 induces the differentiation of myogenic cells into fibrotic cells in injured skeletal muscle: a key event in muscle fibrogenesis. *Am. J. Pathol.* 164:1007-19.

Surendran K., S. P. McCaul, and T. C. Simon, 2002. A role for Wnt-4 in renal fibrosis. *Am. J. Physiol. Renal Physiol.* 282:F431-41.

Thompson M. D., and S. P. Monga, 2007. Wnt/beta-catenin signaling in liver health and disease. *Hepatology* 45:1298-305.

van de Schans V. A., J. F. Smits, and W. M. Blankesteijn, 2008. The Wnt/frizzled pathway in cardiovascular development and disease: Friend or foe? *Eur. J. Pharmacol.*

Barandon L., T. Couffinhal, J. Ezan, P. Dufourcq, P. Costet, P. Alzieu, L. Leroux, C. Moreau, D. Dare, and C. Duplaa (2003). Reduction of infarct size and prevention of cardiac rupture in transgenic mice overexpressing FrzA. *Circulation* 108:2282-2289.

Barker N. and H. Clevers (2006). Mining the Wnt pathway for cancer therapeutics. *Nat. Rev. Drug Discov.* 5:997-1014.

Blankesteijn W. M., Y. P. Essers-Janssen, M. J. Verluyten, M. J. Daemen, and J. F. Smits (1997). A homologue of Drosophila tissue polarity gene frizzled is expressed in migrating myofibroblasts in the infarcted rat heart. *Nat. Med.* 3:541-544.

Blankesteijn W. M., V. A. van de Schans, P. Ter Horst, and J. F. Smits (2008). The Wnt/frizzled/GSK-3beta pathway: a novel therapeutic target for cardiac hypertrophy. *Trends Pharmacol. Sci.* 29:175-180.

Brade T., J. Manner, and M. Kuhl (2006). The role of Wnt signaling in cardiac development and tissue remodeling in the mature heart. *Cardiovasc. Res.* 72:198-209.

Brown R. D., S.K. Ambler, M. D. Mitchell, and C. S. Long (2005). The cardiac fibroblast: therapeutic target in myocardial remodeling and failure. *Annu. Rev. Pharmacol. Toxicol.* 45:657-687.

Cleutjens J. P., W. M. Blankesteijn, M. J. Daemen, and J. F. Smits (1999). The infarcted myocardium: simply dead tissue, or a lively target for therapeutic interventions. *Cardiovasc. Res.* 44:232-241.

Clevers H. (2006). Wnt/beta-catenin signaling in development and disease. *Cell* 127:469-480.

De Ferrari G. V. and R. T. Moon (2006). The ups and downs of Wnt signaling in prevalent neurological disorders. *Oncogene* 25:7545-7553.

DeAlmeida V. I., L. Miao, J. A. Ernst, H. Koeppen, P. Polakis, and B. Rubinfeld (2007). The soluble wnt receptor Frizzled8CRD-hFc inhibits the growth of teratocarcinomas in vivo. *Cancer Res.* 67:5371-5379.

Ertl G. and S. Frantz (2005). Healing after myocardial infarction. *Cardiovasc. Res.* 66:22-32.

Frangogiannis N. G. (2006). The mechanistic basis of infarct healing. *Antioxid Redox Signal* 8:1907-1939.

Hendrickx M. and L. Leyns (2008). Non-conventional Frizzled ligands and Wnt receptors. *Dev. Growth Differ.* 50:229-243.

Hinz B. (2007). Formation and function of the myofibroblast during tissue repair. *J. Invest. Dermatol.* 127:526-537.

Hinz B., S. H. Phan, V. J. Thannickal, A. Galli, M.L. Bochaton-Piallat, and G. Gabbiani (2007). The myofibroblast: one function, multiple origins. *Am. J. Pathol.* 170:1807-1816.

Hutchins G. M. and B. H. Bulkley (1978). Infarct expansion versus extension: two different complications of acute myocardial infarction. Am. *J. Cardiol.* 41:1127-1132.

Janhunen S., H. Laeremans, S. Rensen, J. Smits, and W. Blankesteijn (2009). Characterization of a cardiac fibroblast cell line immortalized with telomerase. *Naunyn Schmiedeberg's Archives of Pharmacology* 379:205.

Jugdutt B. I. (2008). Pleiotropic effects of cardiac drugs on healing post-MI. The good, bad, and ugly. *Heart Fail Rev.* 13:439-452.

Kobayashi K., M. Luo, Y. Zhang, D.C. Wilkes, G. Ge, T. Grieskamp, C. Yamada, T. C. Liu, G. Huang, C. T. Basson, et al. (2009). Secreted Frizzled-related protein 2 is a procollagen C proteinase enhancer with a role in fibrosis associated with myocardial infarction. *Nat. Cell Biol.* 11:46-55.

Lai S. L., A. J. Chien, and R. T. Moon (2009). Wnt/Fz signaling and the cytoskeleton: potential roles in tumorigenesis. *Cell Res.* 19:532-545.

MacDonald B. T., K. Tamai, and X. He (2009). Wnt/beta-catenin signaling: components, mechanisms, and diseases. *Dev. Cell* 17:9-26.

Nelson W. J. and R. Nusse (2004). Convergence of Wnt, beta-catenin, and cadherin pathways. *Science* 303:1483-1487.

Nusse R. (2005). Wnt signaling in disease and in development. *Cell Res.* 15:28-32.

Piters E., E. Boudin, and W. Van Hul (2008). Wnt signaling: a win for bone. *Arch. Biochem. Biophys.* 473:112-116.

Reya T. and H. Clevers (2005). Wnt signaling in stem cells and cancer. *Nature* 434:843-850.

Säfholm A., K. Leandersson, J. Dejmek, C. Kamp Nielsen, B. O. Villoutreix, and T. Andersson (2005). A formylated hexapeptide ligand mimics the ability of Wnt-5a to impair migration of human breast epithelial cells. *J Biol. Chem.* 281:2740-2749.

Schnolzer M., P. Alewood, A. Jones, D. Alewood, and S. B. Kent (1992). In situ neutralization in Boc-chemistry solid phase peptide synthesis. Rapid, high yield assembly of difficult sequences. *Int. J. Pept. Protein Res.* 40:180-193.

Schulte G. and V. Bryja (2007). The Frizzled family of unconventional G-protein-coupled receptors. *Trends Pharmacol. Sci.* 28:518-525.

Squires C.E., G. P. Escobar, J. F. Payne, R. A. Leonardi, D. K. Goshorn, N. J. Sheats, I. M. Mains, J. T. Mingoia, E. C. Flack, and M. L. Lindsey (2005). Altered fibroblast function following myocardial infarction. *J. Mol. Cell Cardiol.* 39:699-707.

Sun Y., M. F. Kiani, A. E. Postlethwaite, and K. T. Weber (2002). Infarct scar as living tissue. *Basic Res. Cardiol.* 97:343-347.

Takahashi-Yanaga F. and T. Sasaguri (2009). Drug Development Targeting the Glycogen Synthase Kinase-3beta (GSK-3beta)-Mediated Signal Transduction Pathway: Inhibitors of the Wnt/beta-Catenin Signaling Pathway as Novel Anticancer Drugs. *J. Pharmacol. Sci.* 109:179-183.

van de Schans V. A., J. F. Smits, and W. M. Blankesteijn (2008). The Wnt/frizzled pathway in cardiovascular development and disease: Friend or foe? *Eur. I Pharmacol.* 585:338-345.

van den Borne S. W., J. Diez, W. M. Blankesteijn, J. W. Verjans, L. Hofstra, and J. Narula (2010). Myocardial remodeling after infarction: the role of myofibroblasts. *Nat. Rev. Cardiol.* 7:30-37.

van den Borne S. W., V. A. van de Schans, A. E. Strzelecka, H. T. Vervoort-Peters, P. M. Lijnen, J. P. Cleutjens, J. F. Smits, M. J. Daemen, B. J. Janssen, and W. M. Blankesteijn (2009). Mouse strain determines the outcome of wound healing after myocardial infarction. *Cardiovasc. Res.* 84:273-282.

van Es J. H. and H. Clevers (2005). Notch and Wnt inhibitors as potential new drugs for intestinal neoplastic disease. *Trends Mol. Med.* 11:496-502.

Wang Y. and J. Nathans (2007). Tissue/planar cell polarity in vertebrates: new insights and new questions. *Development* 134:647-658.

Willems I. E., M. G. Havenith, J. G. De Mey, and M. J. Daemen (1994). The alpha-smooth muscle actin-positive cells in healing human myocardial scars. *Am. J. Pathol.* 145:868-875.

The invention claimed is:

1. A method for treating cardiovascular disease or cardiac remodeling, the method comprising:

administering to a subject in need thereof a composition comprising a linear polypeptide consisting of SEQ ID NO: 7.

2. The method according to claim 1, wherein the cardiovascular disease is myocardial infarction or cardiac hypertrophy.

3. A method of treating liver fibrosis, lung fibrosis, or hypertrophic scarring of the skin after burning injury, the method comprising:

administering to a subject in need thereof a composition comprising a linear polypeptide consisting of SEQ ID NO: 7.

4. A method of improving wound healing, the method comprising:
administering to a subject in need thereof a composition comprising a linear polypeptide consisting of SEQ ID NO: 7.

* * * * *

UNITED STATES PATENT AND TRADEMARK OFFICE
CERTIFICATE OF CORRECTION

PATENT NO. : 8,598,122 B2  
APPLICATION NO. : 13/138537  
DATED : December 3, 2013  
INVENTOR(S) : Wessel Matthijs Blankesteijn, Hilde Laeremans and Tilman Mathias Hackeng It is certified that error appears in the above-identified patent and that said Letters Patent is hereby corrected as shown below:

On the title page:
In ITEM (30) Foreign Application Priority Data
change "09154475" to --09154475.9--

In the specification:
COLUMN 14, LINE 55, change "Table 3))." to --Table 3).--

Signed and Sealed this  
Fifteenth Day of December, 2015

Michelle K. Lee  
*Director of the United States Patent and Trademark Office*